United States Patent
Marotta

(10) Patent No.: US 10,995,136 B2
(45) Date of Patent: May 4, 2021

(54) 14-3-3 ETA ANTIBODIES AND USES THEREOF FOR THE DIAGNOSIS AND TREATMENT OF ARTHRITIS

(71) Applicant: The University of British Columbia, Vancouver (CA)

(72) Inventor: Anthony Marotta, Vancouver (CA)

(*) Notice: Subject to any disclaimer, the term of this patent is extended or adjusted under 35 U.S.C. 154(b) by 384 days.

(21) Appl. No.: 14/798,398

(22) Filed: Jul. 13, 2015

(65) Prior Publication Data

US 2016/0039918 A1    Feb. 11, 2016

Related U.S. Application Data

(63) Continuation of application No. 12/745,235, filed as application No. PCT/CA2008/002094 on Nov. 26, 2008, now Pat. No. 9,079,947.

(60) Provisional application No. 61/077,123, filed on Jun. 30, 2008, provisional application No. 60/990,520, filed on Nov. 27, 2007.

(51) Int. Cl.
*G01N 33/564* (2006.01)
*C07K 16/18* (2006.01)
*G01N 33/68* (2006.01)
*A61K 39/00* (2006.01)

(52) U.S. Cl.
CPC ......... *C07K 16/18* (2013.01); *G01N 33/6893* (2013.01); *A61K 2039/505* (2013.01); *C07K 2317/24* (2013.01); *C07K 2317/33* (2013.01); *C07K 2317/34* (2013.01); *C07K 2317/76* (2013.01); *G01N 33/564* (2013.01); *G01N 2333/47* (2013.01); *G01N 2800/102* (2013.01)

(58) Field of Classification Search
None
See application file for complete search history.

(56) References Cited

U.S. PATENT DOCUMENTS

| | | |
|---|---|---|
| 4,956,281 A | 9/1990 | Wallner et al. |
| 5,948,765 A | 9/1999 | Shaw et al. |
| 5,976,852 A | 11/1999 | Cheng et al. |
| 5,998,149 A | 12/1999 | Hsich et al. |
| 6,596,476 B1 | 7/2003 | Lesniewski et al. |
| 7,011,952 B2 | 3/2006 | Hageman et al. |
| 7,056,677 B2 | 6/2006 | Takahasi et al. |
| 7,101,962 B2 | 9/2006 | Burke et al. |
| 7,171,311 B2 | 1/2007 | Dai et al. |
| 7,396,654 B2 | 7/2008 | Hayes et al. |
| 7,919,262 B2 | 4/2011 | Yacoubian et al. |
| 7,939,272 B2 | 5/2011 | Buck |
| 2003/0119054 A1 | 6/2003 | Mrksich et al. |
| 2004/0152630 A1 | 8/2004 | Fu et al. |
| 2005/0009094 A1 | 1/2005 | Mueller et al. |
| 2005/0042681 A1 | 2/2005 | Van Eyk et al. |
| 2009/0093005 A1 | 4/2009 | Smalley et al. |
| 2010/0016173 A1 | 1/2010 | Nagalla et al. |
| 2011/0052573 A1 | 3/2011 | Marrotta |
| 2012/0077695 A1 | 3/2012 | Ostroff et al. |
| 2012/0101002 A1 | 4/2012 | Riel-Mehan et al. |

FOREIGN PATENT DOCUMENTS

| | | |
|---|---|---|
| JP | 2005-181342 A | 7/2005 |
| WO | WO 1997/33601 A1 | 9/1997 |
| WO | WO 1997/38315 A1 | 10/1997 |
| WO | WO 1998/26293 | 6/1998 |
| WO | WO 1999/46401 | 9/1999 |
| WO | WO 2003/071927 A2 | 9/2003 |
| WO | WO 03/087831 A2 * | 10/2003 |
| WO | WO 2005/053811 | 6/2005 |
| WO | WO 2005/120568 | 12/2005 |
| WO | WO 2006/126008 A2 | 11/2006 |
| WO | WO 2007/128132 | 11/2007 |
| WO | WO 2009/067811 A1 | 6/2009 |
| WO | WO 2009/067820 A1 | 6/2009 |
| WO | WO 2009/137832 A2 | 11/2009 |

OTHER PUBLICATIONS

Goel, M., et al. J. Immunol. 2004;173:7358-7367.*
Poosarla, V. G., et al. Biotech. Bioeng. 2017;114(6):1331-1342.*
U.S. Appl. No. 12/637,730 (U.S. Publication No. 2012-0003665 A1), entitled, "Dissolved Protein Arthritis Markers" filed Dec. 14, 2009, of Aziz Gharhary, et al.
U.S. Appl. No. 12/745,235, entitled, "14-3-3 ETA Antibodies and Uses Thereof for the Diagnosis and Treatment of Arthritis" filed Oct. 1, 2015, issued as U.S. Pat. No. 9,079,947 on Jul. 14, 2015, of Anthony Marotta, et al.
U.S. Appl. No. 14/873,157 (U.S. Publication No. 2016-0185842 A1) entitled, "14-3-3 Antagonists for the Prevention and Treatment of Arthritis" filed Oct. 1, 2015, of Anthony Marotta, et al.
Ausubel, F. et al., "Current Protocols in Molecular Biology", Ch. 1 Immunoassays, pp. 11.0.1-11.3.6, John Wiley & Sons, New York (1998).
Ausubel, F. et al., "Short Protocols in Molecular Biology", Ch. 11 Immunology, pp. 11-4-11-5, John Wiley & Sons, New York (1999).
Boston, P. et al., "Human 14-3-3 Protein:Radioimmunoassay, Tissue Distribution, and Cerebrospinal Fluid Levels in Patients With Neurological Disorders," J. N. Chem. vol. 38, pp. 1475-1482 (1982).
Corconnier et al., "Diagnostic value of anti-RA33 antibody, antikeratin antibody, antiperinuclear factor and antinuclear antibody in early rheumatoid arthritis: comparison with rheumatoid factor," Br. J. Rheumatol., vol. 35, pp. 620-624 (1996).

(Continued)

*Primary Examiner* — G. R. Ewoldt
(74) *Attorney, Agent, or Firm* — Todd A. Lorenz

(57) ABSTRACT

The invention provides anti-14-3-3 eta antibodies that specifically bind to the human 14-3-3 eta protein isoform in its natural configuration while exhibiting selectivity over human 14-3-3 alpha, beta, delta, epsilon, gamma, tau, and zeta protein isoforms. Methods, kits and pharmaceutical compositions comprising said specific anti-14-3-3 eta antibodies are further provided for the diagnosis and treatment of arthritis.

15 Claims, 8 Drawing Sheets

Specification includes a Sequence Listing.

(56) References Cited

OTHER PUBLICATIONS

Da Silva et al., "Safety of low dose glucocorticoid treatment in rheumatoid arthritis: published evidence and prospective trial data," Ann. Rheum Dis., vol. 65, pp. 285-293 (2006).
Firestein, Gary S.,"Rheumatoid Arthritis: Rheumatoid Synovitis and Pannus," Rheumatology, pp. 5/13.1-5/13.5, Mosby, London (1997).
Furst et al., "Consensus Statement: Updated consensus statement on biological agents, specifically tumour necrosis factor α (TNFα) blocking agents and interleukin-1 receptor antagonist (IL-1ra), for the treatment of rheumatic diseases, 2005" Ann. Rheum Dis., vol. 64, pp. iv2-iv14 (2005).
Gabay et al., "Occurrence of antiperinuclear, antikeratin, and anti-RA 33 antibodies in juvenile chronic arthritis," Ann. Rheum. Dis., vol. 52, pp. 785-789 (1993).
Gilbert M. R., "Neurological Complications" in Abeloff MD et al., Clinical Oncology, 3rd Ed., pp. 1213-1246, Churchill Livingstone/Elsevier Press, New York (2004).
Harris E D Jr., "Cytokines, Lymphokines, Growth Factors, and Chemokines," In: Rheumatoid Arthritis. Philadelphia: W.B. Saunders Company, pp. 105-125 (1997).
Harris E D Jr., "History and Epidemiology of Rheumatoid Arthritis: How long has it affected us, and who is at risk?," In: Rheumatoid Arthritis. Philadelphia: W.B. Saunders Company, pp. 121-127 (1997).
Harris E D Jr., "Introduction," In: Rheumatoid Arthritis. Philadelphia: W.B. Saunders Company, pp. xix-xxiii (1997).
Harris E D Jr., "Rheumatoid Synovium: Complex, and More Than the Sum of its Parts. In: Rheumatoid Arthritis," Philadelphia: W.B. Saunders Company, pp. 126-149, (1997).
Harlow, E., and Lane, D., "Antibodies: A Laboratory Manual," pp. 553-612, Cold Spring Harbor Laboratory Press, Cold Spring Harbor (1988).
Harlow, E. and Lane, D., "Antibodies: A Laboratory Manual," Cold Spring Harbor Laboratory Press, Cold Spring Harbor, NY, pp. 23-26 (1988).
Kandpal et al., "Expression of Protein Kinase Regulator Genes in Human Ear and Cloning of a Gamma Subtype of the 14-3-3 Family of Proteins," DNA and Cell Biology, vol. 16(4), pp. 455-462 (1997).
Katz, A. B. et al., "A Partial Catalog of Proteins Secreted by Epidermal Keratinocytes in Culture," J. Invest. Dermatol., vol. 112, pp. 818-821 (1999).
Kim et al., "When does rheumatoid arthritis begin and why do we need to know?," Arthritis. Reheum., vol. 43, pp. 473-484 (2000).
Konttinen et al., "Analysis of 16 Different Matrix Metalloproteinases (MMP-1 to MMP-20) in the Synovial Membrane: different profiles in trauma and rheumatoid arthritis," Ann. Rheum. Dis., vol. 58, pp. 691-697 (1999).
Krensky et al., "Immunomodulators: Immunosuppressive Agents, Tolerogens, and Immunostimulants," in Hardman—10th Ed., pp. 1461-1483, McGraw Hill, New York (2001).
Leite, John—Invitrogen Corporation, Carlsbad, CA, USA, "Protein detection by Mass Spectrometry," www.invitrogen.com/piq., downloaded Jan. 4, 2013.
Lipsky, Peter E., "Rheumatoid Arthritis", in Braunwald—Harrison's Principles of Internal Medicine, 15th Ed., pp. 1928-1937, McGraw Hill, New York (2001).
Lyons et al., "Effective Use of Autoantibody Tests in the Diagnosis of Systemic Autoimmune Disease," Ann. N.Y. Acad. Sci., vol. 1050, pp. 217-228 (2005).
Maksymowych et al., "14-3-3: A rheumatoid arthritis biomarker," Arthritis and Rheumatism, Vo. 63, No. 10, Suppl. 1. Abstract No. 358 (2011).
Maksymowych et al., "Autoantibody to 14-3-3 ETA Is a Novel Biomarker Associated With MRI Inflammation and Radiographic Progression in Axial Spondyloarthritis," Ninth International Congress on Spondyloarthritis, Clinical and Experimental Rheumatology, vol. 32, pp. 765-838 (2014).
Maksymowych et al., "14-3-3η Autoantibodies: Diagnostic Use in Early Rheumatoid Arthritis," The Journal of Rheumatology, vol. 42, pp. 1-9 (2015).
Martin et al., "Subcellular Localisation of 14-3-3 Isoforms in Rat Brain Using Specific Antibodies," J. of Neurochemistry, vol. 63, pp. 2259-2265 (1994).
Megidish et al., "A Novel Sphingosine-dependent Protein Kinas (SDK1) Specifically Phosphorylates Certain Isoforms of 14-3-3 Protein," J. Biol. Chem. vol. 273, No. 34, pp. 21834-21845 (1998).
Molina et al., "Improved Performances of Spot Multiple Peptide Synthesis," Journal of Peptide Application, Synthesis and Analysis, vol. 9, No. 3, pp. 151-155 (1996).
Moore et al., "Specific Acidic Proteins of the Nervous System", in Carson FD, pp. 343-359 (1967).
Moreira et al., "A Combined Proteome and Ultrastructural Localization Analysis of 14-3-3 Proteins in Transformed Human Amnion (AMA) Cells," Molecular & Cellular Proteomics, vol. 7, pp. 1225-1240 (2008).
Plotz, "The autoantibody repertoire: searching for order," Nat. Immunol. Rev., vol. 3, pp. 73-78 (2003).
Poole, A. R., "Cartilage in Health and Disease," in Koopman WJ—Arthritis and Allied Conditions, 14th Ed., pp. 226-284, Williams & Wilkins, Baltimore (2001).
Rosenau et al., "Autoantibodies to Tumor Necrosis Factor in Patients with Rheumatoid Arthritis and Systemic Lupus Erythematosus," J Rheumatol vol. 36, pp. 753-756 (2009).
Sambrook, J., "Molecular Cloning—Protein Interaction Technologies—A Laboratory Manual," pp. 655-688, Cold Spring Harbor Laboratory Press (2001).
Scheiman, James M and Fendrick, A Mark, "Practical approaches to minimizing gastrointestinal and cardiovascular safety concerns with COX-2 inhibitors and NSAIDs," Arth. Res and Therap. vol. 9, Suppl. 4, pp. S23-S29 (2005).
Sjowall et al., "Beware of Antibodies to Dietary Proteins in "Antigen-specific" Immunoassays! Falsely Positive Anticytokine Antibody Tests Due to Reactivity with Bovine Serum Albumin in Rheumatoid Arthritis (The Swedish TIRA Project)," J Rheumatol, vol. 38, pp. 215-220 (2011).
Skogh et al., "Twenty Eight Joint Count Disease Activity Score in Recent Onset Rheumatoid Arthritis Using C Reactive Protein . . . " Ann. Rheum Dis. vol. 62, pp. 681-682 (2003).
Ubl et al., "14-3-3 protein is a component of Lewy bodies in Parkinson's disease—Mutation analysis and association studies of 14-3-3 eta," Molecular Brain Research, vol. 108, pp. 33-39 (2002).
Vincent et al., "High diagnostic value in rheumatoid arthritis of antibodies to the stratum corneum of rat oesophagus epithelium, so-called 'antikeratin antibodies'," Ann. Rheum. Dis., vol. 48, pp. 712-722 (1989).
Wadhwa et al., "Neutralizing antibodies to granulocyte-macrophage colony-stimulating factor, interleukin-1α and interferon-α but not other cytokines in human immunoglobulin preparations," Immunology, vol. 99, pp. 113-123 (2000).
U.S. Appl. No. 12/745,229 (U.S. Publication No. 2011-0027269 A1) entitled, "14-3-3 Antagonists for the Prevention and Treatment of Arthritis" filed Oct. 22, 2010, of Anthony Marotta, et al.
Ahrens, D., et al., "Expression of matrix metalloproteinase 9 (96-kd gelatinase B) in human arthritis," Arthritis & Rheum. 39:1576-1587 (1996).
Bombara, MP, et al., "Cell contact between T cells and synovial firbroblasts causes induction of adhesion molecules and cytokines," J. Leukocyte Biol. 54:339-406 (1993).
Brand, DD., "Rodent models of rheumatoid arthritis," Comp. Med. 55(2):114-122 (2005).
Burger, D., et al., "Imbalance between interstitial collagenase and tissue inhibitor of metalloproteinases 1 in synoviocytes and fibroblasts upon direct contact with stimulated T lymphocytes: involvement of membrane-associated cytokines," Arthritis Rheum. 41(10): 1748-59 (1998).
Chan, TA, et al., "14-3-3Sigma is required to prevent mitotic catastrophe after DNA damage," Nature 401:616-620 (1999).
Cho, ML, et al., "Effector function of type II collegen-stimulated T cells from rheumatoid arthritis patients: cross-talk between T cells and synovial fibroblasts," Arthritis Rheum. 50(3):776-784 (2004).

(56) References Cited

OTHER PUBLICATIONS

Craparo, A, et al., "14-3-3 (ε) Interacts with the insulin-like growth factor I receptor and insulin receptor substrate I in a phosphoserine-dependent manner," J. Biol. Chem. 272(17): 11663-69 (1997).
Di Fede, G, et al., "The ε isoform of 14-3-3 protein is a componenet of the prion protein amyloid deposits of Gerstmann-Sträussler-Scheinker Disease," J. Neuropathology and Experimental Neurolcigy 66(2):124-130 (2007).
Du, et al., "Association of a phospholipase $A_2$ (14-3-3 protein) with the platelet glycoprotein Ib-IX Complex," J. Biol. Chem. 269(28):18287-18290.
Frank, R., et al., "Spot synthesis: An easy technique for the positionally addressable, parallel chemical synthesis on a membrane support," Tetrahedron 48: 9217-9232 (1992).
Fu, H., et al., "14-3-3 proteins: structure, function and regluation," Annu. Rev. Pharmacol. Toxicol. 40:617-647 (2000).
Ghahary, A, et al., "Keratinocyte-releaseable stratifin functions as a potent collagenase-stimulationg factor in fibroblasts," J. Invest. Dermatol. 122:1188-1197 (2004).
Hermeking, H., et al., "14-3-3σ is a p53-regulated inhibitor of G2/M progression," Mol. Cell 1:3-11 (1997).
Hopp, T.P., and Woods, "Prediction of protein antigenic determinants from amino acid sequences," K.R. Proc. Nat'l. Acad. Sci., USA, 1981;78(6):3824-3828.
Hsich, G, et al., "The 14-3-3 brain protein in cerebrospinal fluid as a marker for transmissible spongiform encephalopathies," N. Engl. J. Med. 335:924-30 (1996).
Ichimura, T, et al., "Brain 14-3-3 protein is an activator protein that activates tryptophan 5-monooxynease in the presence of $Ca^{2+}$, calmodulin-dependent protein kinase II," FEBS Lett. 219:79-82 (1987).
Ichimura, T, et al., "Molecular cloning of cDNA coding for brain-specific 14-3-3 protein, a protein kinase-dependent activator of tyrosine and tryptophan hydroxylases," Proc. Natl. Acad. Sci. USA 85:7084-8 (1988).
Jamal, et al., "Increased expression of human type IIa secretory phospholipase $A_2$ antigen in arthritic synovium," Ann. Rheum. Dis. 57:550-558 (1998).
Jasser, MZ, et al., "Induction of stromelysin-1 and collagenase synthesis in fibrochondrocytes by tumor necrosis factor-alpha," Matrix Biology 14:241 (1994).
Jiang, J, et al., "Multifunctional proteins bridge mitosis with motility and cancer with inflammation and arthritis," The Scientific World Journal 10:1244-1257 (2010).
Katrib, A., et al., "What can we learn from the synovium in early rheumatoid arthritis?" Inflamm. Res. 51(4):170-175 (2002).
Kilani, R, et al ., "Detection of high levels of 2 specific isoforms of 14-3-3 proteins in synovial fluid from patients with joint infimattion," J. Rheum. 34: 1650-1657 (2007).
Kohler, et al., "Continuous cultures of fused cells secreting antibody of predefined specificity," Nature 256: 495-497 (1975).
Konttinen, YT, et al., "New collagenolytic enzymes identified at the pannus-hard tissue junction in rheumatoid arthritis: destruction from above," Matrix Biol. 17(8-9):585-601 (1998).
Laronga, C, et al., "Association of the cyclin-dependent kinases and 14-3-3 sigma negatively regulates cell cycel progression," J. Biol. Chem. 275(30):23016-23112 (2000).
Lindy, O., et al., "Matrix metalloproteinase 13 (collagenase 3) in human rheumatoid synovium," Arthritis Rheum. 40(8):1391-1399 (1997).
Ma, M., et al., "Enhanced production of mouse hybridomas to picomoles of antigen using EL-4 conditioned media with an in vitro immunization protocol," In Vitro 20(9):739 (1984).
Martin, H, et al., "Antibodies against the major brain isoforms of 14-3-3 protein. An antibody specific for the N-acetylated amino-terminus of a protein," FEBS Letters 331(3):296-303 (1993).
McInnes, IB, et al., "Cell-cell interactions in synovitis interactions between T lymphocytes and synovials cells," Arthritis Research, 2(5):374-8.34 (2000).

Miranda-Carús, ME, et al., "IL-15 and the initiation of cell contact-dependent synovial fibroblast-T lymphocyte cross-talk in rheumatoid arthritis: effect of methotrexate," J. Immunol. 173:1463-1476 (2004).
Moore, et al., "Nutrition and Lysosomal Activity. The influence of vitamin E deficiency and its duration on the stability of lysosomes in the kidneys of rats," Biochem. J. 103:923 (1967).
Neeck, G, et al., "Involvement of the glucocorticoid receptor in the pathogenesis of rheumatoid arthritis," Ann. New York Academy of Sciences 966:491-495 (2002).
Pap, T., et al., "Differential expression pattern of membrane-type matrix metalloproteinases in rheumatoid arthritis," Arthritis Rheum. 43(6):1226-1232 (2000).
Sakaguchi, S., et al., "Animal models of arthritis caused by systemic alteration of the immune system," Curr. Opin. Immunol. 17(6):589-594 (2005).
Sato, S, et al., "14-3-3η is a novel regulator of parkin ubiquitin ligase," The Embo Journal, 25:211-221 (2006).
Satoh, J, et al., "The 14-3-3 protein ε isoform expressed in reactive astrocytes in demyelinating lesions of multiple sclerosis binds to vimentin and glial fibrillary acidic protein in culture human astrocytes," Amer. J. of Pathology 165:577-592 (2004).
Smeets, TJ, et al., "The effects of interferon-beta treatment of synovial inflammation and expression of metalloproteinases with rheumatoid arthritis," Arthritis Rheum. 43(2):270-274 (2000).
Sorsa, T., et al., "Collagenase in synovitis of rheumatoid arthritis," Arthritis Rheum. 22:44-53 (1992).
Takashashi, S, et al., "Functional interaction of the immunosuppressant mizoribine with the 14-3-3 protein," Biochemical and Biophysical Research Communications 274:87-92 (2000).
Tohyama, et al., "Localization of human glucocorticoid receptor in rheumatoid synovial tissue of the knee joint," Scandanavian J. Rheum. 34:426-432 (2005).
Toker, A., et al., "Protein kinase C inhibitor proteins. Purification from sheep brain and sequence similarity to lipocortins and 14-3-3 protein," Eur. J. Biochem. 191(2):421-429 (1990).
Tolboom, TCA, et al., "Invasive properties of fibroblast-like synoviocytes: correlation with growth characteristics and expression of MMP-1, MMP-3, and MMP-10," Ann. Rheum. Dis. 61:975-980 (2002).
Umahara, T, et al., "Intranuclear localization and isoform-dependent translocation of 14-3-3 proteins in human brain with infarction," J. Neurology Sciences 260:159-166 (2007).
Van Everbroeck, BRJ, et al., "14-3-3 γ-isoform detection distinguishes sporadic Creutzfeldt-Jakob disease from other dementias," J. Neurology Neurosurgery and Psychiatry 76:100-102 (2005).
Vierboom, MP, et al., "Preclinical models of arthritic disease in non-human primates," Drug Discovery Today 12:327-335 (2007).
Wang, B, et al., "Isolation of high-affinity peptide antagonists of 14-3-3 proteins by phage display," Biochemistry 38:12499-12504 (1999).
Wilker, E., et al., "14-3-3 Proteins—a focus on cancer and human disease," J. Mo. Cell Cardiol. 37(3):633-642 (2004).
Williams, RO, "Collagen-induced arthritis as a model for rheumatoid arthritis," Methods Mol. Med. 98:207-16 (2004).
Xiao, et al., "An approach to studying lung cancer-related proteins in human blood," Molecular & Cellular Proteomics 4:1480-86 (2005).
Yaffe, MB, "How dow 14-3-3 proteins work?—Gatekeeper pohsphorylation and the molecular anvil hypothesis," FEBS Lett. 513(1):53-57 (2002).
Yamamura, Y, et al., "Effector function of resting T cells: activation of synovial fibroblasts," J. Immunol. 166:2270-2275 (2001).
Yao, Q., et al., "Intra-articular injection of recominbant TRAIL induces synovial apoptosis and reduces inflammation in a rabbit knee model of arthritis," Arthritis Research and Therapy 8:R16 (2006).
Yoon Kim Suk, et al., "Role of the 14-3-3η as a positive regulator of the glucocorticoid receptor transcriptional activation," Endocrinology 146: 3133-3140 (2005).

(56) References Cited

OTHER PUBLICATIONS

Wakabayashi et al., "Increased concentrations of 14-3-3ε, γ and ζ isoforms in cerebrospinal fluid of AIDS patients with neuronal destruction," Clinica Chimica Acta, 312(1-2): pp. 97-105 (2001).

* cited by examiner

```
14-3-3gamma       -MVDREQLVQKARLAEQAERYDDMAAAMKNVTELNEPLSNEERNLLSVAYKNVVGARRSS  59
14-3-3eta         -MGDREQLLQRARLAEQAERYDDMASAMKAVTELNEPLSNEDRNLLSVAYKNVVGARRSS  59
14-3-3alpha/beta  MTMDKSELVQKAKLAEQAERYDDMAAAMKAVTEQGHELSNEERNLLSVAYKNVVGARRSS  60
14-3-3zeta        --MDKNELVQKAKLAEQAERYDDMAACMKSVTEQGAELSNEERNLLSVAYKNVVGARRSS  58
14-3-3theta       --MEKTELIQKAKLAEQAERYDDMATCMKAVTEQGAELSNEERNLLSVAYKNVVGGRRSA  58
14-3-3sigma       --MERASLIQKAKLAEQAERYEDMAAFMKGAVEKGEELSCEERNLLSVAYKNVVGGQRAA  58
14-3-3epsilon     -MDDREDLVYQAKLAEQAERYDEMVESMKKVAGMDVELTVEERNLLSVAYKNVIGARRAS  59
                   :  .*: :*;********;:*.  **  ..  .  *;  *;:***********;*.;*:;

14-3-3gamma       WRVISSIEQKTSADGNEKKIEMVRAYREKIEKELEAVCQDVLSLLDNYLIKNCSETQYES 119
14-3-3eta         WRVISSIEQKTMADGNEKKLEKVKAYREKIEKELETVCNDVLSLLDKFLIKNCNDFQYES 119
14-3-3alpha/beta  WRVISSIEQKT--ERNEKKQQMGKEYREKIEAELQDICNDVLELLDKYLIPNATQP--ES 116
14-3-3zeta        WRVVSSIEQKT--EGAEKKQQMAREYREKIETELRDICNDVLSLLEKFLIPNASQA--ES 114
14-3-3theta       WRVISSIEQKT--DTSDKKLQLIKDYREKVESELRSICTTVLELLDKYLIANATNP--ES 114
14-3-3sigma       WRVLSSIEQKSNEEGSEEKGPEVREYREKVETELQGVCDTVLGLLDSHLIKEAGDA--ES 116
14-3-3epsilon     WRIISSIEQKEENKGGEDKLKMIREYRQMVETELKLICCDILDVLDKHLIPAANTG--ES 117
                  **::******    .  :.*    ; **; :* **. :*  :*  :*:...**   .   **

14-3-3gamma       KVFYLKMKGDYYRYLAEVATGEKRATVVESSEKAYSEAHEISKEHMQPTHPIRLGLALNY 179
14-3-3eta         KVFYLKMKGDYYRYLAEVASGEKKNSVVEASEAAYKEAFEISKEQMQPTHPIRLGLALNF 179
14-3-3alpha/beta  KVFYLKMKGDYFRYLSEVASGDNKQTTVSNSQQAYQEAFEISKKEMQPTHPIRLGLALNF 176
14-3-3zeta        KVFYLKMKGDYYRYLAEVAAGDDKKGIVDQSQQAYQEAFEISKKEMQPTHPIRLGLALNF 174
14-3-3theta       KVFYLKMKGDYYRYLAEVACGDDRKQTIDNSQGAYQEAFDISKKEMQPTHPIRLGLALNF 174
14-3-3sigma       RVFYLKMKGDYYRYLAEVATGDDKKRIIDSARSAYQEAMDISKKEMPPTNPIRLGLALNF 176
14-3-3epsilon     KVFYYKMKGDYHRYLAEFATGNDRKEAAENSLVAYKAASDIAMTELPPTHPIRLGLALNF 177
                  :***  ******.***:*.*  *::        :  **. * :*:   .: **:**********;

14-3-3gamma       SVFYYEIQNAPEQACHLAKTAFDDAIAELDTLNEDSYKDSTLIMQLLRDNLTLWTSDQQD 239
14-3-3eta         SVFYYEIQNAPEQACLLAKQAFDDAIAELDTLNEDSYKDSTLIMQLLRDNLTLWTSDQQD 239
14-3-3alpha/beta  SVFYYEILNSPEKACSLAKTAFDEAIAELDTLNEESYKDSTLIMQLLRDNLTLWTSENQG 236
14-3-3zeta        SVFYYEILNSPEKACSLAKTAFDEAIAELDTLSEESYKDSTLIMQLLRDNLTLWTSDTQG 234
14-3-3theta       SVFYYEILNNPELACTLAKTAFDEAIAELDTLNEDSYKDSTLIMQLLRDNLTLWTSDSAG 234
14-3-3sigma       SVFHYEIANSPEEAISLAKTTFDEAMADLHTLSEDSYKDSTLIMQLLRDNLTLWTADNAG 236
14-3-3epsilon     SVFYYEILNSPDRACRLAKAAFDDAIAELDTLSEESYKDSTLIMQLLRDNLTLWTSDMQG 237
                  ***:***  *  * * :***  :**.:*;*.**.*:********************::  .

14-3-3gamma       DDG---GEGNN------- 247
14-3-3eta         EEA---GEGN-------- 246
14-3-3alpha/beta  DEG-DAGEG-EN------ 246
14-3-3zeta        DEA-EAGEGGEN------ 245
14-3-3theta       EEC-DAAEGAEN------ 245
14-3-3sigma       EEGGEAPQEPQS------ 248
14-3-3epsilon     DGEEQNKEALQDVEDENQ 255
                  :       :
```

FIG. 4

Lane: 1 2 3 4 5 6 7 8

Lane: 1  2  3  4  5  6

Lane: 1 2 3 4 5 6

SEQUENCE LISTING

```
<160> NUMBER OF SEQ ID NOS: 63

<210> SEQ ID NO 1
<211> LENGTH: 15
<212> TYPE: PRT
<213> ORGANISM: Homo sapiens

<400> SEQUENCE: 1

Leu Glu Thr Val Cys Asn Asp Val Leu Ser Leu Leu Asp Lys Phe
1               5                   10                  15

<210> SEQ ID NO 2
<211> LENGTH: 9
<212> TYPE: PRT
<213> ORGANISM: Homo sapiens

<400> SEQUENCE: 2

Glu Gln Ala Cys Leu Leu Ala Lys Gln
1               5

<210> SEQ ID NO 3
<211> LENGTH: 12
<212> TYPE: PRT
<213> ORGANISM: Homo sapiens

<400> SEQUENCE: 3

Asn Ser Val Val Glu Ala Ser Glu Ala Ala Tyr Lys
1               5                   10

<210> SEQ ID NO 4
<211> LENGTH: 9
<212> TYPE: PRT
<213> ORGANISM: Homo sapiens

<400> SEQUENCE: 4

Asn Ser Val Val Glu Ala Ser Glu Ala
1               5

<210> SEQ ID NO 5
<211> LENGTH: 9
<212> TYPE: PRT
<213> ORGANISM: Homo sapiens

<400> SEQUENCE: 5

Val Glu Ala Ser Glu Ala Ala Tyr Lys
1               5

<210> SEQ ID NO 6
<211> LENGTH: 8
<212> TYPE: PRT
<213> ORGANISM: Homo sapiens

<400> SEQUENCE: 6

Glu Gln Met Gln Pro Thr His Pro
1               5
```

```
<210> SEQ ID NO 7
<211> LENGTH: 10
<212> TYPE: PRT
<213> ORGANISM: Homo sapiens

<400> SEQUENCE: 7

Thr His Pro Ile Arg Leu Gly Leu Ala Leu
1               5                   10

<210> SEQ ID NO 8
<211> LENGTH: 11
<212> TYPE: PRT
<213> ORGANISM: Homo sapiens

<400> SEQUENCE: 8

Val Lys Ala Tyr Thr Glu Lys Ile Glu Lys Glu
1               5                   10

<210> SEQ ID NO 9
<211> LENGTH: 12
<212> TYPE: PRT
<213> ORGANISM: Homo sapiens

<400> SEQUENCE: 9

Gln Lys Thr Met Ala Asp Gly Asn Glu Lys Lys Leu
1               5                   10

<210> SEQ ID NO 10
<211> LENGTH: 9
<212> TYPE: PRT
<213> ORGANISM: Homo sapiens

<400> SEQUENCE: 10

Ala Ser Gly Glu Lys Lys Asn Ser Val
1               5

<210> SEQ ID NO 11
<211> LENGTH: 9
<212> TYPE: PRT
<213> ORGANISM: Homo sapiens

<400> SEQUENCE: 11

Lys Thr Met Ala Asp Gly Asn Glu Lys
1               5

<210> SEQ ID NO 12
<211> LENGTH: 9
<212> TYPE: PRT
<213> ORGANISM: Homo sapiens

<400> SEQUENCE: 12

Glu Leu Asn Glu Pro Leu Ser Asn Glu
1               5

<210> SEQ ID NO 13
<211> LENGTH: 15
<212> TYPE: PRT
<213> ORGANISM: Homo sapiens

<400> SEQUENCE: 13

Leu Leu Asp Lys Phe Leu Ile Lys Asn Cys Asn Asp Phe Gln Tyr
1               5                   10                  15

<210> SEQ ID NO 14
```

```
<211> LENGTH: 14
<212> TYPE: PRT
<213> ORGANISM: Homo sapiens

<400> SEQUENCE: 14

Tyr Tyr Arg Tyr Leu Ala Glu Val Ala Ser Gly Glu Lys Lys
1               5                   10

<210> SEQ ID NO 15
<211> LENGTH: 11
<212> TYPE: PRT
<213> ORGANISM: Homo sapiens

<400> SEQUENCE: 15

Tyr Glu Ile Gln Asn Ala Pro Glu Gln Ala Cys
1               5                   10

<210> SEQ ID NO 16
<211> LENGTH: 13
<212> TYPE: PRT
<213> ORGANISM: Homo sapiens

<400> SEQUENCE: 16

Ala Glu Leu Asp Thr Leu Asn Glu Asp Ser Tyr Lys Asp
1               5                   10

<210> SEQ ID NO 17
<211> LENGTH: 14
<212> TYPE: PRT
<213> ORGANISM: Homo sapiens

<400> SEQUENCE: 17

Leu Leu Ser Val Ala Tyr Lys Asn Val Val Gly Ala Arg Arg
1               5                   10

<210> SEQ ID NO 18
<211> LENGTH: 9
<212> TYPE: PRT
<213> ORGANISM: Homo sapiens

<400> SEQUENCE: 18

Glu Gln Ala Glu Arg Tyr Asp Asp Met
1               5

<210> SEQ ID NO 19
<211> LENGTH: 9
<212> TYPE: PRT
<213> ORGANISM: Homo sapiens

<400> SEQUENCE: 19

Tyr Tyr Arg Tyr Leu Ala Glu Val Ala
1               5

<210> SEQ ID NO 20
<211> LENGTH: 8
<212> TYPE: PRT
<213> ORGANISM: Homo sapiens

<400> SEQUENCE: 20

Glu Ser Lys Val Phe Tyr Leu Lys
1               5

<210> SEQ ID NO 21
<211> LENGTH: 9
<212> TYPE: PRT
```

<213> ORGANISM: Homo sapiens

<400> SEQUENCE: 21

Thr Leu Asn Glu Asp Ser Tyr Lys Asp
1               5

<210> SEQ ID NO 22
<211> LENGTH: 8
<212> TYPE: PRT
<213> ORGANISM: Homo sapiens

<400> SEQUENCE: 22

Lys Lys Leu Glu Lys Val Lys Ala
1               5

<210> SEQ ID NO 23
<211> LENGTH: 11
<212> TYPE: PRT
<213> ORGANISM: Homo sapiens

<400> SEQUENCE: 23

Glu Lys Lys Leu Arg Lys Val Lys Ala Tyr Arg
1               5                   10

<210> SEQ ID NO 24
<211> LENGTH: 17
<212> TYPE: PRT
<213> ORGANISM: Homo sapiens

<400> SEQUENCE: 24

Lys Lys Asn Ser Val Val Glu Ala Ser Glu Ala Ala Tyr Lys Glu Ala
1               5                   10                  15

Phe

<210> SEQ ID NO 25
<211> LENGTH: 16
<212> TYPE: PRT
<213> ORGANISM: Homo sapiens

<400> SEQUENCE: 25

Asp Lys Phe Leu Ile Lys Asn Cys Asn Asp Phe Gln Tyr Glu Ser Lys
1               5                   10                  15

<210> SEQ ID NO 26
<211> LENGTH: 10
<212> TYPE: PRT
<213> ORGANISM: Homo sapiens

<400> SEQUENCE: 26

Gln Gln Asp Glu Glu Ala Gly Glu Gly Asn
1               5                   10

<210> SEQ ID NO 27
<211> LENGTH: 9
<212> TYPE: PRT
<213> ORGANISM: Homo sapiens

<400> SEQUENCE: 27

Asn Glu Lys Lys Leu Glu Lys Val Lys
1               5

<210> SEQ ID NO 28
<211> LENGTH: 13
<212> TYPE: PRT

-continued

<213> ORGANISM: Homo sapiens

<400> SEQUENCE: 28

Leu Asp Lys Phe Leu Ile Lys Asn Cys Asn Asp Phe Gln
1               5                   10

<210> SEQ ID NO 29
<211> LENGTH: 6
<212> TYPE: PRT
<213> ORGANISM: Homo sapiens

<400> SEQUENCE: 29

Glu Lys Lys Asn Ser Val
1               5

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu Asp Lys Phe Leu Ile Lys Asn Ser Asn Asp Phe
1               5                   10

<210> SEQ ID NO 31
<211> LENGTH: 10
<212> TYPE: PRT
<213> ORGANISM: Homo sapiens

<400> SEQUENCE: 31

Lys Lys Leu Glu Lys Val Lys Ala Tyr Arg
1               5                   10

<210> SEQ ID NO 32
<211> LENGTH: 15
<212> TYPE: PRT
<213> ORGANISM: Homo sapiens

<400> SEQUENCE: 32

Lys Asn Ser Val Val Glu Ala Ser Glu Ala Ala Tyr Lys Glu Ala
1               5                   10                  15

<210> SEQ ID NO 33
<211> LENGTH: 12
<212> TYPE: PRT
<213> ORGANISM: Homo sapiens

<400> SEQUENCE: 33

Asp Arg Glu Gln Leu Leu Gln Arg Ala Arg Leu Ala
1               5                   10

<210> SEQ ID NO 34
<211> LENGTH: 247
<212> TYPE: PRT
<213> ORGANISM: Homo sapiens

<400> SEQUENCE: 34

Met Val Asp Arg Glu Gln Leu Val Gln Lys Ala Arg Leu Ala Glu Gln
1               5                   10                  15

Ala Glu Arg Tyr Asp Asp Met Ala Ala Ala Met Lys Asn Val Thr Glu
                20                  25                  30

-continued

```
Leu Asn Glu Pro Leu Ser Asn Glu Arg Asn Leu Leu Ser Val Ala
             35                  40                  45

Tyr Lys Asn Val Val Gly Ala Arg Arg Ser Ser Trp Arg Val Ile Ser
 50                  55                  60

Ser Ile Glu Gln Lys Thr Ser Ala Asp Gly Asn Glu Lys Lys Ile Glu
 65                  70                  75                  80

Met Val Arg Ala Tyr Arg Glu Lys Ile Glu Lys Leu Glu Ala Val
                 85                  90                  95

Cys Gln Asp Val Leu Ser Leu Leu Asp Asn Tyr Leu Ile Lys Asn Cys
                100                 105                 110

Ser Glu Thr Gln Tyr Glu Ser Lys Val Phe Tyr Leu Lys Met Lys Gly
                115                 120                 125

Asp Tyr Tyr Arg Tyr Leu Ala Glu Val Ala Thr Gly Glu Lys Arg Ala
            130                 135                 140

Thr Val Val Glu Ser Ser Glu Lys Ala Tyr Ser Glu Ala His Glu Ile
145                 150                 155                 160

Ser Lys Glu His Met Gln Pro Thr His Pro Ile Arg Leu Gly Leu Ala
                165                 170                 175

Leu Asn Tyr Ser Val Phe Tyr Tyr Glu Ile Gln Asn Ala Pro Glu Gln
                180                 185                 190

Ala Cys His Leu Ala Lys Thr Ala Phe Asp Asp Ala Ile Ala Glu Leu
            195                 200                 205

Asp Thr Leu Asn Glu Asp Ser Tyr Lys Asp Ser Thr Leu Ile Met Gln
    210                 215                 220

Leu Leu Arg Asp Asn Leu Thr Leu Trp Thr Ser Asp Gln Gln Asp Asp
225                 230                 235                 240

Asp Gly Gly Glu Gly Asn Asn
                245

<210> SEQ ID NO 35
<211> LENGTH: 246
<212> TYPE: PRT
<213> ORGANISM: Homo sapiens

<400> SEQUENCE: 35

Met Gly Asp Arg Glu Gln Leu Leu Gln Arg Ala Arg Leu Ala Glu Gln
 1               5                  10                  15

Ala Glu Arg Tyr Asp Asp Met Ala Ser Ala Met Lys Ala Val Thr Glu
                20                  25                  30

Leu Asn Glu Pro Leu Ser Asn Glu Asp Arg Asn Leu Leu Ser Val Ala
             35                  40                  45

Tyr Lys Asn Val Val Gly Ala Arg Arg Ser Ser Trp Arg Val Ile Ser
 50                  55                  60

Ser Ile Glu Gln Lys Thr Met Ala Asp Gly Asn Glu Lys Lys Leu Glu
 65                  70                  75                  80

Lys Val Lys Ala Tyr Arg Glu Lys Ile Glu Lys Glu Leu Glu Thr Val
                 85                  90                  95

Cys Asn Asp Val Leu Ser Leu Leu Asp Lys Phe Leu Ile Lys Asn Cys
                100                 105                 110

Asn Asp Phe Gln Tyr Glu Ser Lys Val Phe Tyr Leu Lys Met Lys Gly
                115                 120                 125

Asp Tyr Tyr Arg Tyr Leu Ala Glu Val Ala Ser Gly Glu Lys Lys Asn
            130                 135                 140

Ser Val Val Glu Ala Ser Glu Ala Ala Tyr Lys Glu Ala Phe Glu Ile
145                 150                 155                 160
```

```
Ser Lys Glu Gln Met Gln Pro Thr His Pro Ile Arg Leu Gly Leu Ala
                165                 170                 175

Leu Asn Phe Ser Val Phe Tyr Tyr Glu Ile Gln Asn Ala Pro Glu Gln
            180                 185                 190

Ala Cys Leu Leu Ala Lys Gln Ala Phe Asp Asp Ala Ile Ala Glu Leu
        195                 200                 205

Asp Thr Leu Asn Glu Asp Ser Tyr Lys Asp Ser Thr Leu Ile Met Gln
    210                 215                 220

Leu Leu Arg Asp Asn Leu Thr Leu Trp Thr Ser Asp Gln Gln Asp Glu
225                 230                 235                 240

Glu Ala Gly Glu Gly Asn
                245

<210> SEQ ID NO 36
<211> LENGTH: 246
<212> TYPE: PRT
<213> ORGANISM: Homo sapiens

<400> SEQUENCE: 36

Met Thr Met Asp Lys Ser Glu Leu Val Gln Lys Ala Lys Leu Ala Glu
1               5                   10                  15

Gln Ala Glu Arg Tyr Asp Asp Met Ala Ala Met Lys Ala Val Thr
            20                  25                  30

Glu Gln Gly His Glu Leu Ser Asn Glu Glu Arg Asn Leu Leu Ser Val
        35                  40                  45

Ala Tyr Lys Asn Val Val Gly Ala Arg Arg Ser Ser Trp Arg Val Ile
    50                  55                  60

Ser Ser Ile Glu Gln Lys Thr Glu Arg Asn Glu Lys Lys Gln Gln Met
65                  70                  75                  80

Gly Lys Glu Tyr Arg Glu Lys Ile Glu Ala Glu Leu Gln Asp Ile Cys
                85                  90                  95

Asn Asp Val Leu Glu Leu Leu Asp Lys Tyr Leu Ile Pro Asn Ala Thr
            100                 105                 110

Gln Pro Glu Ser Lys Val Phe Tyr Leu Lys Met Lys Gly Asp Tyr Phe
        115                 120                 125

Arg Tyr Leu Ser Glu Val Ala Ser Gly Asp Asn Lys Gln Thr Thr Val
    130                 135                 140

Ser Asn Ser Gln Gln Ala Tyr Gln Glu Ala Phe Glu Ile Ser Lys Lys
145                 150                 155                 160

Glu Met Gln Pro Thr His Pro Ile Arg Leu Gly Leu Ala Leu Asn Phe
                165                 170                 175

Ser Val Phe Tyr Tyr Glu Ile Leu Asn Ser Pro Glu Lys Ala Cys Ser
            180                 185                 190

Leu Ala Lys Thr Ala Phe Asp Glu Ala Ile Ala Glu Leu Asp Thr Leu
        195                 200                 205

Asn Glu Glu Ser Tyr Lys Asp Ser Thr Leu Ile Met Gln Leu Leu Arg
    210                 215                 220

Asp Asn Leu Thr Leu Trp Thr Ser Glu Asn Gln Gly Asp Glu Gly Asp
225                 230                 235                 240

Ala Gly Glu Gly Glu Asn
                245

<210> SEQ ID NO 37
<211> LENGTH: 245
<212> TYPE: PRT
```

<213> ORGANISM: Homo sapiens

<400> SEQUENCE: 37

Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Ala Arg Arg Ser Ser Trp Arg Val Val Ser Ser
    50                  55                  60

Ile Glu Gln Lys Thr Glu Gly Ala Glu Lys Lys Gln Gln Met Ala Arg
65                  70                  75                  80

Glu Tyr Arg Glu Lys Ile Glu Thr Glu Leu Arg Asp Ile Cys Asn Asp
                85                  90                  95

Val Leu Ser Leu Leu Glu Lys Phe Leu Ile Pro Asn Ala Ser Gln Ala
            100                 105                 110

Glu Ser Lys Val Phe Tyr Leu Lys Met Lys Gly Asp Tyr Tyr Arg Tyr
        115                 120                 125

Leu Ala Glu Val Ala Ala Gly Asp Asp Lys Lys Gly Ile Val Asp Gln
    130                 135                 140

Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Ser Glu
        195                 200                 205

Glu Ser Tyr Lys Asp Ser Thr Leu Ile Met Gln Leu Leu Arg Asp Asn
    210                 215                 220

Leu Thr Leu Trp Thr Ser Asp Thr Gln Gly Asp Glu Ala Glu Ala Gly
225                 230                 235                 240

Glu Gly Gly Glu Asn
                245

<210> SEQ ID NO 38
<211> LENGTH: 245
<212> TYPE: PRT
<213> ORGANISM: Homo sapiens

<400> SEQUENCE: 38

Met Glu Lys Thr Glu Leu Ile Gln Lys Ala Lys Leu Ala Glu Gln Ala
1               5                   10                  15

Glu Arg Tyr Asp Asp Met Ala Thr Cys Met Lys Ala Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Gly Arg Arg Ser Ala Trp Arg Val Ile Ser Ser
    50                  55                  60

Ile Glu Gln Lys Thr Asp Thr Ser Asp Lys Lys Leu Gln Leu Ile Lys
65                  70                  75                  80

Asp Tyr Arg Glu Lys Val Glu Ser Glu Leu Arg Ser Ile Cys Thr Thr
                85                  90                  95

Val Leu Glu Leu Leu Asp Lys Tyr Leu Ile Ala Asn Ala Thr Asn Pro

```
            100                 105                 110
Glu Ser Lys Val Phe Tyr Leu Lys Met Lys Gly Asp Tyr Phe Arg Tyr
        115                 120                 125
Leu Ala Glu Val Ala Cys Gly Asp Arg Lys Gln Thr Ile Asp Asn
    130                 135                 140
Ser Gln Gly Ala Tyr Gln Ala Phe Asp Ile Ser Lys Lys Glu Met
145                 150                 155                 160
Gln Pro Thr His Pro Ile Arg Leu Gly Leu Ala Leu Asn Phe Ser Val
            165                 170                 175
Phe Tyr Tyr Glu Ile Leu Asn Asn Pro Glu Leu Ala Cys Thr Leu Ala
        180                 185                 190
Lys Thr Ala Phe Asp Glu Ala Ile Ala Glu Leu Asp Thr Leu Asn Glu
    195                 200                 205
Asp Ser Tyr Lys Asp Ser Thr Leu Ile Met Gln Leu Leu Arg Asp Asn
210                 215                 220
Leu Thr Leu Trp Thr Ser Asp Ser Ala Gly Glu Glu Cys Asp Ala Ala
225                 230                 235                 240
Glu Gly Ala Glu Asn
            245

<210> SEQ ID NO 39
<211> LENGTH: 248
<212> TYPE: PRT
<213> ORGANISM: Homo sapiens

<400> SEQUENCE: 39

Met Glu Arg Ala Ser Leu Ile Gln Lys Ala Lys Leu Ala Glu Gln Ala
1               5                   10                  15
Glu Arg Tyr Glu Asp Met Ala Ala Phe Met Lys Gly Ala Val Glu Lys
            20                  25                  30
Gly Glu Glu Leu Ser Cys Glu Glu Arg Asn Leu Leu Ser Val Ala Tyr
        35                  40                  45
Lys Asn Val Val Gly Gly Gln Arg Ala Ala Trp Arg Val Leu Ser Ser
    50                  55                  60
Ile Glu Gln Lys Ser Asn Glu Glu Gly Ser Glu Glu Lys Gly Pro Glu
65                  70                  75                  80
Val Arg Glu Tyr Arg Glu Lys Val Glu Thr Glu Leu Gln Gly Val Cys
            85                  90                  95
Asp Thr Val Leu Gly Leu Leu Asp Ser His Leu Ile Lys Glu Ala Gly
        100                 105                 110
Asp Ala Glu Ser Arg Val Phe Tyr Leu Lys Met Lys Gly Asp Tyr Tyr
    115                 120                 125
Arg Tyr Leu Ala Glu Val Ala Thr Gly Asp Asp Lys Lys Arg Ile Ile
130                 135                 140
Asp Ser Ala Arg Ser Ala Tyr Gln Glu Ala Met Asp Ile Ser Lys Lys
145                 150                 155                 160
Glu Met Pro Pro Thr Asn Pro Ile Arg Leu Gly Leu Ala Leu Asn Phe
            165                 170                 175
Ser Val Phe His Tyr Glu Ile Ala Asn Ser Pro Glu Glu Ala Ile Ser
        180                 185                 190
Leu Ala Lys Thr Thr Phe Asp Glu Ala Met Ala Asp Leu His Thr Leu
    195                 200                 205
Ser Glu Asp Ser Tyr Lys Asp Ser Thr Leu Ile Met Gln Leu Leu Arg
210                 215                 220
```

-continued

```
Asp Asn Leu Thr Leu Trp Thr Ala Asp Asn Ala Gly Glu Glu Gly Gly
225                 230                 235                 240

Glu Ala Pro Gln Glu Pro Gln Ser
                245

<210> SEQ ID NO 40
<211> LENGTH: 255
<212> TYPE: PRT
<213> ORGANISM: Homo sapiens

<400> SEQUENCE: 40

Met Asp Asp Arg Glu Asp Leu Val Tyr Gln Ala Lys Leu Ala Glu Gln
1               5                   10                  15

Ala Glu Arg Tyr Asp Glu Met Val Glu Ser Met Lys Lys Val Ala Gly
                20                  25                  30

Met Asp Val Glu Leu Thr Val Glu Glu Arg Asn Leu Leu Ser Val Ala
            35                  40                  45

Tyr Lys Asn Val Ile Gly Ala Arg Arg Ala Ser Trp Arg Ile Ile Ser
50                  55                  60

Ser Ile Glu Gln Lys Glu Glu Asn Lys Gly Gly Glu Asp Lys Leu Lys
65                  70                  75                  80

Met Ile Arg Glu Tyr Arg Gln Met Val Glu Thr Leu Lys Leu Ile
                85                  90                  95

Cys Cys Asp Ile Leu Asp Val Leu Asp Lys His Leu Ile Pro Ala Ala
            100                 105                 110

Asn Thr Gly Glu Ser Lys Val Phe Tyr Tyr Lys Met Lys Gly Asp Tyr
        115                 120                 125

His Arg Tyr Leu Ala Glu Phe Ala Thr Gly Asn Asp Arg Lys Glu Ala
130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Asp Arg Ala Cys
            180                 185                 190

Arg Leu Ala Lys Ala Ala Phe Asp Asp Ala Ile Ala Glu Leu Asp Thr
        195                 200                 205

Leu Ser Glu Glu Ser Tyr Lys Asp Ser Thr Leu Ile Met Gln Leu Leu
210                 215                 220

Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
                245                 250                 255

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide derived from human 14-3-3 eta residues
      104-115

<400> SEQUENCE: 41

Cys Leu Asp Lys Phe Leu Ile Lys Asn Ser Asn Asp Phe
1               5                   10

<210> SEQ ID NO 42
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide derived from human 14-3-3 eta residues
      77-86

<400> SEQUENCE: 42

Lys Lys Leu Glu Lys Val Lys Ala Tyr Arg Cys
1               5                   10

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide derived from human 14-3-3 eta residues
      143-157

<400> SEQUENCE: 43

Cys Lys Asn Ser Val Val Glu Ala Ser Glu Ala Ala Tyr Lys Glu Ala
1               5                   10                  15

<210> SEQ ID NO 44
<211> LENGTH: 4
<212> TYPE: PRT
<213> ORGANISM: Homo sapiens

<400> SEQUENCE: 44

Cys Leu Asp Lys
1

<210> SEQ ID NO 45
<211> LENGTH: 4
<212> TYPE: PRT
<213> ORGANISM: Homo sapiens

<400> SEQUENCE: 45

Lys Lys Leu Glu
1

<210> SEQ ID NO 46
<211> LENGTH: 4
<212> TYPE: PRT
<213> ORGANISM: Homo sapiens

<400> SEQUENCE: 46

Cys Lys Asn Ser
1

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide epitope derived from N-terminus of
      14-3-3 eta
<220> FEATURE:
<223> OTHER INFORMATION: N-term acetylated
<220> FEATURE:
<223> OTHER INFORMATION: C-term amidated

<400> SEQUENCE: 47

Asp Arg Glu Gln Leu Leu Gln Arg Ala Arg Leu Ala
1               5                   10
```

<210> SEQ ID NO 48
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gcgaattcct gcagcgggcg cggctggccg a                          31

<210> SEQ ID NO 49
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gctcgagcct gaaggatctt cagttgcctt c                          31

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
agaattcagt tgccttctcc tgctt                                 25

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
acatatgggg gaccggga                                         18

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
agaattctta attgttgcct tcgccg                                26

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
acatatggtg gaccgcgagc                                       20

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
acatatgaca atggataaaa gtgagctg                                        28

<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
agaattctta gttctctccc tccccagc                                        28

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
acatatggat gatcgagagg atctg                                           25

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
agaattctca ctgattttcg tcttccac                                        28

<210> SEQ ID NO 58
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
acatatggag agagccagtc tgatcc                                          26

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
agaattcagc tctggggctc ctg                                             23

```
<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
acatatggag aagactgagc tgatcc                                          26

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
agaattctta gttttcagcc ccttctgc                                        28

<210> SEQ ID NO 62
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
acatatggat aaaaatgagc tggttc                                          26

<210> SEQ ID NO 63
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
agaattctta attttcccct ccttctcct                                       29
```

14-3-3 ETA ANTIBODIES AND USES THEREOF FOR THE DIAGNOSIS AND TREATMENT OF ARTHRITIS

CROSS-REFERENCE TO RELATED APPLICATIONS

This application is a divisional of U.S. Non-Provisional patent application Ser. No. 12/745,235, filed Oct. 22, 2010, and claims the benefit of U.S. Provisional Patent Application Ser. No. 60/990,520, filed 27 Nov. 2007, and U.S. Provisional Patent Application Ser. No. 61/077,123, filed 30 Jun. 2008, which are expressly incorporated herein in their entirety by reference.

SEQUENCE LISTING

The instant application contains a Sequence Listing which has been submitted in ASCII format via EFS-Web and is hereby incorporated by reference in its entirety. Said ASCII copy, created on May 22, 2013, is named 177071-PCT-US SL.txt and is 26,156 bytes in size.

FIELD

The invention pertains to antibodies that specifically bind to the eta isoform of 14-3-3 protein and are capable of discriminating between the eta isoform and other 14-3-3 protein isoforms.

BACKGROUND 14-3-3 proteins are a family of conserved intracellular regulatory molecules that are ubiquitously expressed in eukaryotes. 14-3-3 proteins have the ability to bind a multitude of functionally diverse signaling proteins, including kinases, phosphatases, and transmembrane receptors. Indeed, more than 100 signaling proteins have been reported as 14-3-3 ligands. 14-3-3 proteins may be considered evolved members of the Tetratrico Peptide Repeat superfamily. They generally have 9 or 10 alpha helices, and usually form homo- and/or hetero-dimer interactions along their amino-termini helices. These proteins contain a number of known domains, including regions for divalent cation interaction, phosphorylation & acetylation, and proteolytic cleavage, among others. There are seven distinct genetically encoded isoforms of the 14-3-3 proteins that are known to be expressed in mammals, with each isoform comprising between 242-255 amino acids. The seven 14-3-3 protein isoforms are designated as 14-3-3 α/β (alpha/beta), 14-3-3 δ/ξ (delta/zeta), 14-3-3 ε (epsilon), 14-3-3 γ (gamma), 14-3-3 η (eta), 14-3-3 τ/θ (tau/theta), and 14-3-3 σ (sigma/stratifin).

14-3-3 proteins have a high degree of sequence similarity. Consequently, anti-14-3-3 antibodies typically recognize more than one 14-3-3 protein isoform. Several anti-14-3-3 antibody preparations that have been characterized are commercially available. For example, rabbit polyclonal antibodies that recognize 14-3-3 protein are available from Biomol, Santa Cruz Biotechnology, Upstate Biotechnology, and Assay Designs. These polyclonal antibody preparations recognize 14-3-3 eta in some form; however none are selective for the eta isoform over other 14-3-3 protein isoforms. See also Martin, H. et al., (1993) Antibodies against the major brain isoforms of 14-3-3 protein. FEBS 331:296-303. See also WO 2007/128132 filed 9 May 2007. In addition to lacking isoform selectivity, few 14-3-3 antibodies have been shown to recognize 14-3-3 protein in its native configuration.

14-3-3 proteins have been implicated in a variety of conditions. However, the ubiquity and functional diversity of 14-3-3 proteins largely precludes therapeutic application of antibodies that bind to multiple 14-3-3 protein isoforms ("pan 14-3-3 antibodies") and/or are incapable of recognizing 14-3-3 protein in its native configuration. Moreover, particular 14-3-3 isoforms are implicated in particular conditions, which pan 14-3-3 antibodies may not confidently detect in diagnostic assays and which may not be treatable in a targeted manner by such pan 14-3-3 antibodies. For example, 14-3-3 eta and 14-3-3 gamma have been implicated in arthritis. See WO 2007/128132 filed 9 May 2007. See also Kilani et al. (2007, J. Rheum. 34: 1650-1657; WO 2007/128132) who have reported that two members of the 14-3-3 protein family, particularly 14-3-3 eta and 14-3-3 gamma, are present within the synovial fluid and serum of patients with arthritis, and these isoforms are directly correlated with the levels of MMP-1 and MMP-3 in the synovial fluid and serum.

SUMMARY OF INVENTION

The present invention stems in part from the surprising finding that antibodies selective for the eta isoform of 14-3-3 protein in its native configuration may be made using select epitopes of 14-3-3 eta, despite the high degree of sequence identity between 14-3-3 isoforms. In particular, the present invention provides anti-14-3-3 protein antibodies that (i) bind specifically to the 14-3-3 eta protein in its native configuration, as evidenced by, for example, immunoprecipitation, and (ii) bind selectively to 14-3-3 eta protein over other 14-3-3 protein isoforms. This combination of qualities distinguishes antibodies of the present invention from the prior art and provides for the use of selective anti-14-3-3 eta antibodies in diagnostic and therapeutic methods directed to conditions in which 14-3-3 eta is implicated.

Accordingly, in one aspect, the invention provides anti-14-3-3 eta antibodies. The anti-14-3-3 antibodies of the invention are capable of (i) binding specifically to human 14-3-3 eta protein in its native configuration, as evidenced by, for example, immunoprecipitation of native 14-3-3 eta, and (ii) binding selectively to human 14-3-3 eta protein over other human 14-3-3 protein isoforms.

In a preferred embodiment, an anti-14-3-3 eta antibody of the invention is capable of binding to 14-3-3 eta protein that is aberrantly localized in the extracellular synovial space in arthritis.

In a preferred embodiment, an anti-14-3-3 eta antibody of the invention does not bind to an epitope located at the N-terminus of the human 14-3-3 eta protein.

In a preferred embodiment, an anti-14-3-3 eta antibody of the invention is capable of binding to an epitope comprising a peptide selected from the group consisting of 14-3-3 eta loop peptides, 14-3-3 eta helix peptides, and 14-3-3 eta non-helix peptides, with eta loop peptides being especially preferred.

In a preferred embodiment, the 14-3-3 eta loop peptide comprises an amino acid sequence selected from the group consisting of SEQ ID NOs:11-16. In another embodiment, an anti-14-3-3 eta antibody binds to a region of 14-3-3 eta that overlaps with an amino acid sequence corresponding to a sequence selected from the group consisting of SEQ ID NOs:11-16.

In a preferred embodiment, the 14-3-3 eta helix peptide comprises an amino acid sequence selected from the group consisting of SEQ ID NOs:1-10. In another embodiment, an anti-14-3-3 eta antibody binds to a region of 14-3-3 eta that overlaps with an amino acid sequence corresponding to a sequence selected from the group consisting of SEQ ID NOs:1-10.

In a preferred embodiment, the 14-3-3 eta non-helix peptide comprises an amino acid sequence selected from the group consisting of SEQ ID NOs:17-32. In another embodiment, an anti-14-3-3 eta antibody binds to a region of 14-3-3 eta that overlaps with an amino acid sequence corresponding to a sequence selected from the group consisting of SEQ ID NOs:17-32.

In an especially preferred embodiment, an anti-14-3-3 eta antibody of the invention binds to an amino acid sequence selected from the group consisting of LDKFLIKNSNDF (SEQ ID NO:30), KKLEKVKAYR (SEQ ID NO:31), and KNSVVEASEAAYKEA (SEQ ID NO:32).

Exemplary 14-3-3 eta loop, helix, and non-helix peptides are disclosed in Table 1 herein. Notably, SEQ ID NO:30 varies from corresponding 14-3-3 eta sequence in that a cysteine occurring in 14-3-3 eta sequence has been replaced by serine to avoid disulfide bond formation. In one embodiment, the invention provides antibodies that also bind to the natural 14-3-3 sequence correlate of SEQ ID NO:30 comprising a cysteine. In one embodiment, the invention provides antibodies capable of binding to peptide sequences that vary from those listed in Table 1 by substitution of serine for cysteine.

Exemplary 14-3-3 eta loop, helix, and non-helix peptides are disclosed in Table 1 herein. Notably, SEQ ID NO:30 varies from corresponding 14-3-3 eta sequence in that a cysteine occurring in 14-3-3 eta sequence has been replaced by serine to avoid disulfide bond formation. In one embodiment, the invention provides antibodies that also bind to the natural 14-3-3 sequence correlate of SEQ ID NO:30 comprising a cysteine. In one embodiment, the invention provides antibodies capable of binding to peptide sequences that vary from those listed in Table 1 by substitution of serine for cysteine.

In one embodiment, an anti-14-3-3 eta antibody is capable of inhibiting the induction of MMP by 14-3-3 eta. Preferably, the MMP is selected from the group consisting of MMP-1, 3, 8, 9, 10, 11 and 13, with MMP-1 and MMP-3 being especially preferred.

In one aspect, the invention provides methods for diagnosing diseases and conditions that involve 14-3-3 eta. The methods comprise using an anti-14-3-3 eta antibody of the invention to detect an alteration in 14-3-3 eta protein, e.g., a change in expression, localization, function, etc. In one embodiment, detection involves immunoprecipitation with an anti-14-3-3 eta antibody of the invention. In one embodiment, detection involves the use of ELISA employing an anti-14-3-3 eta antibody of the invention. In one embodiment, detection involves Western blotting using an anti-14-3-3 eta antibody of the invention. In one embodiment, detection involves the use of an anti-14-3-3 eta antibody of the invention in immunohistochemistry. In one embodiment, detection involves the use of an anti-14-3-3 eta antibody of the invention in immunofluorescence. In one embodiment, detection involves the use of an anti-14-3-3 eta antibody of the invention in FACS analysis. In one embodiment, detection involves the use of an anti-14-3-3 eta antibody of the invention in radioimmunoassay. In one embodiment, detection involves the use of an anti-14-3-3 eta antibody of the invention in a strip test. In one embodiment, detection involves the use of an anti-14-3-3 eta antibody of the invention in a point of care test. In one embodiment, detection of 14-3-3 eta is combined with detection of another marker of the condition (e.g., MMP for arthritis).

In one embodiment, the invention provides methods for diagnosing inflammatory conditions. In a preferred embodiment, methods for diagnosing arthritis are provided. Included are methods for diagnosing a disease selected from the group consisting of ankylosing spondylitis, Behçet's Disease, diffuse idiopathic skeletal hyperostosis (DISH), Ehlers-Danlos Syndrome (EDS), Felty's Syndrome, fibromyalgia, gout, infectious arthritis, juvenile arthritis, lupus, mixed connective tissue disease (MCTD), osteoarthritis, Paget's Disease, polymyalgia rheumatica, polymyositis and dermatomyositis, pseudogout, psoriatic arthritis, Raynaud's Phenomenon, reactive arthritis, rheumatoid arthritis, scleroderma, Sjögren's Syndrome, Still's Disease, and Wegener's granulomatosis.

In one embodiment, the methods involve detecting 14-3-3 eta protein in the synovial fluid, plasma, or serum of a patient. In one embodiment, detection is done by immunoprecipitation of 14-3-3 eta protein from synovial fluid, plasma, or serum using an anti-14-3-3 eta antibody of the invention. In one embodiment, detection involves the use of ELISA employing an anti-14-3-3 eta antibody of the invention. In one embodiment, detection involves Western blotting of a sample comprising synovial fluid, plasma, or serum from a patient using an anti-14-3-3 eta antibody of the invention. In one embodiment, detection involves the use of radioimmunoassay. In one embodiment, detection involves the use of a strip test. In one embodiment, detection involves the use of a point of care test. In one embodiment, detection of 14-3-3 eta is combined with detection of another marker of arthritis (e.g., MMP, anti-CCP, anti-RF and/or CRP).

In one embodiment the invention provides methods for diagnosing neurological conditions. In a preferred embodiment, methods for diagnosing a disease selected from the group consisting of bacterial meningitis and Creutzfeldt Jakob disease are provided.

In one aspect, the invention provides methods for treating diseases that involve 14-3-3 eta. The methods comprise administering a therapeutically effective amount of an anti-14-3-3 eta antibody of the invention to a patient. In some embodiments, the methods comprise combination treatments.

In one embodiment, the invention provides methods of treating an inflammatory condition. In a preferred embodiment, methods for treating arthritis are provided. Included are methods of treating a disease selected from the group consisting of ankylosing spondylitis, Behçet's Disease, diffuse idiopathic skeletal hyperostosis (DISH), Ehlers-Danlos Syndrome (EDS), Felty's Syndrome, fibromyalgia, gout, infectious arthritis, juvenile arthritis, lupus, mixed connective tissue disease (MCTD), osteoarthritis, Paget's Disease, polymyalgia rheumatica, polymyositis and dermatomyositis, pseudogout, psoriatic arthritis, Raynaud's Phenomenon, reactive arthritis, rheumatoid arthritis, scleroderma, Sjögren's Syndrome, Still's Disease, and Wegener's granulomatosis.

In one embodiment, the method involves a combination treatment, wherein at least one other therapeutic agent is administered in addition to one or more anti-14-3-3 eta antibodies of the invention. In a preferred embodiment, the therapeutic agent is selected from the group consisting of disease-modifying antirheumatic drugs (DMARDs), disease modifying osteoarthritis drugs (DMOADs; for example, see Loeser, Reumatologia, 21:104-106, 2005), anti-TNFα antibody, anti-IL-1 antibody, anti-CD4 antibody, anti-CTLA4 antibody, anti-CD20 antibody, anti-IL-6 antibody, leflunomide, sulfasalazine, and methotrexate.

In one aspect, the invention provides prophylactic methods for preventing the development of conditions involving 14-3-3 eta.

In one embodiment, the invention provides prophylactic methods for preventing the development of an inflammatory condition in a subject at risk of developing an inflammatory condition. In a preferred embodiment, prophylactic methods for preventing arthritis in a subject at risk of developing arthritis are provided. Included are prophylactic methods for preventing a disease selected from the group consisting of ankylosing spondylitis, Behçet's Disease, diffuse idiopathic skeletal hyperostosis (DISH), Ehlers-Danlos Syndrome (EDS), Felty's Syndrome, fibromyalgia, gout, infectious arthritis, juvenile arthritis, lupus, mixed connective tissue disease (MCTD), osteoarthritis, Paget's Disease, polymyalgia rheumatica, polymyositis and dermatomyositis, pseudogout, psoriatic arthritis, Raynaud's Phenomenon, reactive arthritis, rheumatoid arthritis, scleroderma, Sjögren's Syndrome, Still's Disease, and Wegener's granulomatosis. The methods comprise administering to the subject an anti-14-3-3 eta antibody of the invention. In one embodiment the anti-14-3-3 eta antibody is administered as a component of a combination therapy described herein.

In one aspect, the invention provides methods for monitoring treatment of a disease involving 14-3-3 eta. The methods involve determining the level of 14-3-3 eta in patient samples using an anti-14-3-3 eta antibody of the invention and monitoring the level of 14-3-3 eta in a patient undergoing treatment.

In one embodiment, the invention provides methods for monitoring treatment of an inflammatory condition. In a preferred embodiment, methods for monitoring the treatment of arthritis are provided. Included are methods for monitoring the treatment of a disease selected from the group consisting of ankylosing spondylitis, Behçet's Disease, diffuse idiopathic skeletal hyperostosis (DISH), Ehlers-Danlos Syndrome (EDS), Felty's Syndrome, fibromyalgia, gout, infectious arthritis, juvenile arthritis, lupus, mixed connective tissue disease (MCTD), osteoarthritis, Paget's Disease, polymyalgia rheumatica, polymyositis and dermatomyositis, pseudogout, psoriatic arthritis, Raynaud's Phenomenon, reactive arthritis, rheumatoid arthritis, scleroderma, Sjögren's Syndrome, Still's Disease, and Wegener's granulomatosis.

In one aspect, the invention provides methods for determining the response potential of a patient to treatment directed at a disease involving 14-3-3 eta. In one embodiment, the methods involve determining the level of 14-3-3 eta in a patient sample using an anti-14-3-3 eta antibody of the invention. In a preferred embodiment, the level of 14-3-3 eta in the patient sample is compared to that of samples from subjects whose ability to respond to treatment is known.

In one embodiment, the invention provides methods for determining the response potential of a patient to treatment directed at an inflammatory condition. In a preferred embodiment, methods for determining the response potential of a patient to treatment directed at arthritis are provided. Included are methods for determining the response potential to treatment of a disease selected from the group consisting of ankylosing spondylitis, Behçet's Disease, diffuse idiopathic skeletal hyperostosis (DISH), Ehlers-Danlos Syndrome (EDS), Felty's Syndrome, fibromyalgia, gout, infectious arthritis, juvenile arthritis, lupus, mixed connective tissue disease (MCTD), osteoarthritis, Paget's Disease, polymyalgia rheumatica, polymyositis and dermatomyositis, pseudogout, psoriatic arthritis, Raynaud's Phenomenon, reactive arthritis, rheumatoid arthritis, scleroderma, Sjögren's Syndrome, Still's Disease, and Wegener's granulomatosis.

In one aspect, the invention provides methods for distinguishing between subtypes of diseases involving 14-3-3 eta.

In one embodiment, methods for distinguishing between subtypes of inflammatory disorders. In a preferred embodiment methods for distinguishing between subtypes of arthritis are provided. Included are methods for differentiating between groups consisting of ankylosing spondylitis, Behçet's Disease, diffuse idiopathic skeletal hyperostosis (DISH), Ehlers-Danlos Syndrome (EDS), Felty's Syndrome, fibromyalgia, gout, infectious arthritis, juvenile arthritis, lupus, mixed connective tissue disease (MCTD), osteoarthritis, Paget's Disease, polymyalgia rheumatica, polymyositis and dermatomyositis, pseudogout, psoriatic arthritis, Raynaud's Phenomenon, reactive arthritis, rheumatoid arthritis, scleroderma, Sjögren's Syndrome, Still's Disease, and Wegener's granulomatosis. In one embodiment, the methods involve determining the level of 14-3-3 eta in a patient sample using an anti-14-3-3 eta antibody of the invention. In a preferred embodiment, the level of 14-3-3 eta in the patient is compared to that of samples from subjects whose subtype of inflammatory disorder or prognosis is known.

In one aspect, the invention provides methods for reducing the damage to a joint injured by trauma. The methods comprise administering an anti-14-3-3 eta antibody of the invention to a subject having a joint injured by trauma. In one embodiment the anti-14-3-3 eta antibody is administered as a component of a combination therapy described herein.

In one aspect, the invention provides methods of decreasing MMP expression. In one embodiment, the MMP expression to be decreased is in the synovium. The methods comprise delivering an anti-14-3-3 eta antibody of the invention to a tissue or compartment in which MMP producing cells are present, wherein the MMP producing cells are responsive to 14-3-3 eta protein. Delivery may be direct to the affected tissue or compartment, or indirect. In a preferred embodiment, the responsive cells are fibroblasts or FLS cells.

In a preferred embodiment, the MMP expression that is to be decreased is MMP expression that is associated with arthritis.

In a preferred embodiment, the MMP expression that is to be decreased is that of an MMP selected from the group consisting of MMP-1, 3, 8, 9, 10, 11 and 13. In an especially preferred embodiment, the MMP expression that is to be decreased is that of MMP-1 or MMP-3.

In one aspect, the invention provides methods of inhibiting MMP induction by 14-3-3 eta protein. Inhibition may be partial or complete. The methods comprise delivering an anti-14-3-3 eta antibody of the invention to a tissue or compartment in which MMP producing cells are present, wherein the MMP producing cells are responsive to 14-3-3 eta protein. Delivery may be direct to the affected tissue or compartment, or indirect. In a preferred embodiment, the anti-14-3-3 eta antibody is administered to the synovium. In a preferred embodiment, the responsive cells are fibroblasts or FLS cells.

In a preferred embodiment, the MMP induction that is to be inhibited is that of an MMP which is upregulated in arthritis.

In a preferred embodiment, the MMP induction that is to be inhibited is that of an MMP selected from the group consisting of MMP-1, 3, 8, 9, 10, 11 and 13. In an especially preferred embodiment, the MMP induction that is to be inhibited is that of MMP-1 or MMP-3.

In one aspect, the invention provides methods of decreasing joint swelling in a subject. The methods comprise administering an anti-14-3-3 eta antibody of the invention to an affected subject.

In one aspect, the invention provides methods of decreasing cartilage degradation in a subject. The methods comprise administering an anti-14-3-3 eta antibody of the invention to an affected subject.

In one aspect, the invention provides methods of decreasing bone degradation in a subject. The methods comprise administering an anti-14-3-3 eta antibody of the invention to an affected subject.

In one aspect, the invention provides methods of decreasing pro-inflammatory cytokine accumulation in synovial fluid. The methods comprise administering an anti-14-3-3 eta antibody of the invention to an affected subject.

For methods involving administration of an anti-14-3-3 eta antibody to an affected subject, in a preferred embodiment, intracapsular delivery is used. In another embodiment, systemic delivery is used. The therapeutic compositions are formulated and administration is such that the anti-14-3-3 eta antibody so delivered is available to engage extracellularly localized 14-3-3 eta protein.

In one aspect, the invention provides kits useful for diagnosing a condition involving 14-3-3 eta or determining the prognosis of a patient affected by a condition involving 14-3-3 eta.

In one aspect, the invention provides pharmaceutical compositions useful for the treatment of diseases involving 14-3-3 eta. The pharmaceutical compositions comprise an anti-14-3-3 eta antibody of the invention. In a preferred embodiment, pharmaceutical compositions useful for the treatment of arthritis are provided.

In one aspect, the invention provides methods for producing a medicament useful for the treatment of a condition involving 14-3-3 eta.

BRIEF DESCRIPTION OF THE DRAWINGS

FIG. 4. Sequence alignment for various 14-3-3 protein isoforms SEQ ID NOS 34-40, respectively, in order of appearance).

DETAILED DESCRIPTION

Figure 1:
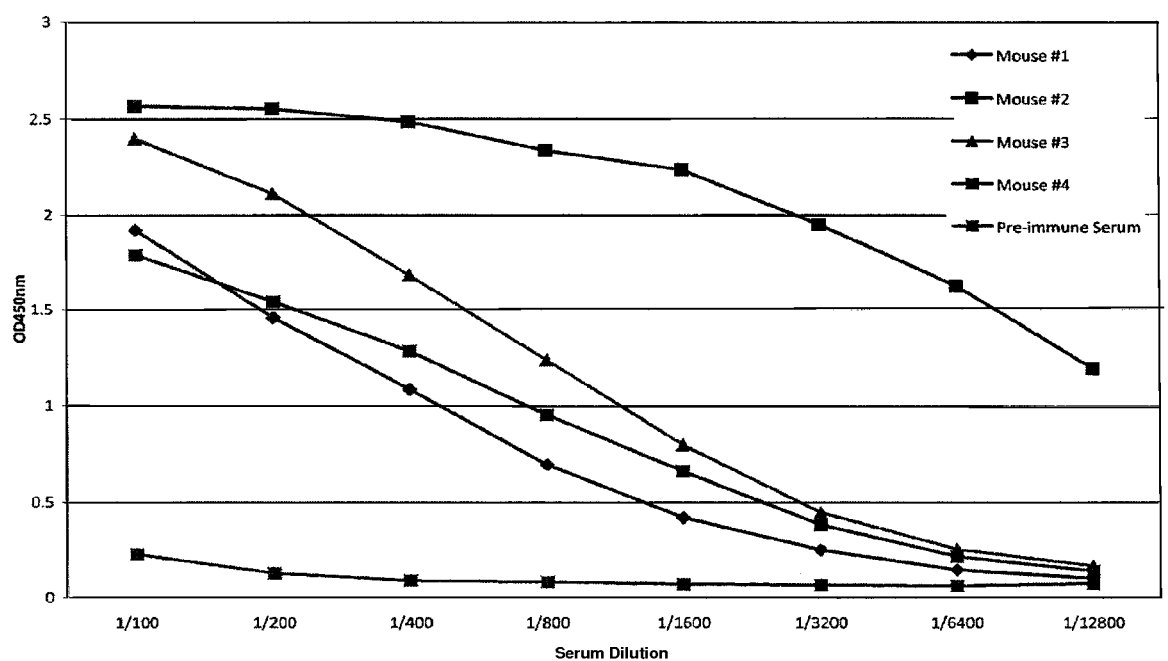
FIG. 1. ELISA: Test Bleed Titration of Mouse Anti-AUG1-CLDK Immune Serum (after 2nd boost) on AUG1-CLDK-BSA Antigen (IgG response only)('CLDK' disclosed as SEQ ID NO: 44).

An antibody, or antigen-binding fragment thereof, is said to "specifically bind," "immunologically bind," and/or is "immunologically reactive" if it reacts at a detectable level (within, for example, an ELISA assay) with ligand, and does not react detectably with unrelated ligands under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties can be quantified using methods well known in the art. For example, see Davies et al. (1990) Annual Rev. Biochem. 59:439-473.

"Antibody" refers to a composition comprising a protein that binds specifically to a corresponding antigen and has a common, general structure of immunoglobulins. The term antibody specifically covers polyclonal antibodies, monoclonal antibodies, dimers, multimers, multispecific antibodies (e.g., bispecific antibodies), and antibody fragments, so long as they exhibit the desired biological activity. Antibodies may be murine, human, humanized, chimeric, or derived from other species. Typically, an antibody will comprise at least two heavy chains and two light chains interconnected by disulfide bonds, which when combined form a binding domain that interacts with an antigen. Each heavy chain is comprised of a heavy chain variable region (VH) and a heavy chain constant region (CH). The heavy chain constant region is comprised of three domains, CH1, CH2 and CH3, and may be of the mu, delta, gamma, alpha or epsilon isotype. Similarly, the light chain is comprised of a light chain variable region (VL) and a light chain constant region (CL). The light chain constant region is comprised of one domain, CL, which may be of the kappa or lambda isotype. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The heavy chain constant region mediates binding of the immunoglobulin to host tissue or host factors, particularly through cellular receptors such as the Fc receptors (e.g., FcγRI, FcγRII, FcγRIII, etc.). As used herein, antibody also includes an antigen binding portion of an immunoglobulin that retains the ability to bind antigen. These include, as examples, F(ab), a monovalent fragment of VL CL and VH CH antibody domains; and F(ab')₂ fragment, a bivalent fragment comprising two Fab fragments linked by a disulfide bridge at the hinge region. The term antibody also refers to recombinant single chain Fv fragments (scFv) and bispecific molecules such as, e.g., diabodies, triabodies, and tetrabodies (see, e.g., U.S. Pat. No. 5,844,094).

Antibodies may be produced and used in many forms, including antibody complexes. As used herein, the term "antibody complex" refers to a complex of one or more antibodies with another antibody or with an antibody fragment or fragments, or a complex of two or more antibody fragments. Antibody complexes include multimeric forms of anti-14-3-3 antibodies such as homoconjugates and heteroconjugates as well as other cross-linked antibodies as described herein.

"Antigen" is to be construed broadly and refers to any molecule, composition, or particle that can bind specifically to an antibody. An antigen has one or more epitopes that interact with the antibody, although it does not necessarily induce production of that antibody.

The terms "cross-linked", "cross-linking" and grammatical equivalents thereof, refer to the attachment of two or more antibodies to form antibody complexes, and may also be referred to as multimerization. Cross-linking or multimerization includes the attachment of two or more of the same antibodies (e.g. homodimerization), as well as the attachment of two or more different antibodies (e.g. heterodimerization). Those of skill in the art will also recognize that cross-linking or multimerization is also referred to as forming antibody homoconjugates and antibody heteroconjugates. Such conjugates may involve the attachment of two or more monoclonal antibodies of the same clonal origin (homoconjugates) or the attachment of two or more antibodies of different clonal origin (also referred to as heteroconjugates or bispecific). Antibodies may be crosslinked by non-covalent or covalent attachment. Numerous techniques suitable for cross-linking will be appreciated by those of skill in the art. Non-covalent attachment may be achieved through the use of a secondary antibody that is specific to the primary antibody species. For example, a goat anti-mouse (GAM) secondary antibody may be used to cross-link a mouse monoclonal antibody. Covalent attachment may be achieved through the use of chemical cross-linkers.

"Epitope" refers to a determinant capable of specific binding to an antibody. Epitopes are chemical features generally present on surfaces of molecules and accessible to interaction with an antibody. Typical chemical features are amino acids and sugar moieties, having three-dimensional structural characteristics as well as chemical properties including charge, hydrophilicity, and lipophilicity. Conformational epitopes are distinguished from non-conformational epitopes by loss of reactivity with an antibody following a change in the spatial elements of the molecule without any change in the underlying chemical structure.

"Humanized antibody" refers to an immunoglobulin molecule containing a minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. A humanized antibody will also encompass immunoglobulins comprising at least a portion of an immunoglobulin constant region (Fc), generally that of a human immunoglobulin (Jones et al., Nature 321:522-525 (1986); Reichmann et al, Nature 332:323-329 (1988)).

"Immunogen" refers to a substance, compound, or composition which stimulates the production of an immune response.

The term "immunoglobulin locus" refers to a genetic element or set of linked genetic elements that comprise information that can be used by a B cell or B cell precursor to express an immunoglobulin polypeptide. This polypeptide can be a heavy chain polypeptide, a light chain polypeptide, or the fusion of a heavy and a light chain polypeptide. In the case of an unrearranged locus, the genetic elements are assembled by a B cell precursor to form the gene encoding an immunoglobulin polypeptide. In the case of a rearranged locus, a gene encoding an immunoglobulin polypeptide is contained within the locus.

"Isotype" refers to an antibody class defined by its heavy chain constant region. Heavy chains are generally classified as gamma, mu, alpha, delta, epsilon and designated as IgG, IgM, IgA, IgD, and IgE. Variations within each isotype are categorized into subtypes, for example subtypes of IgG are divided into IgG1, IgG2, IgG3, and IgG4, while IgA is divided into IgA1 and IgA2. The IgY isotype is specific to birds.

"Monoclonal antibody" or "monoclonal antibody composition" refers to a preparation of antibody molecules of single molecular composition. A monoclonal antibody composition displays a single binding specificity and affinity for a particular epitope.

The term "human monoclonal antibody" includes antibodies displaying a single binding specificity which have variable and/or constant regions (if present) derived from human immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene, fused to an immortalized cell.

"Single chain Fv" or "scFv" refers to an antibody comprising the VH and VL regions of an antibody, wherein these domains are present in a single polypeptide chain. Generally, an scFv further comprises a polypeptide linker between the VH and VL domains which enables the scFv to form the desired structure for antigen binding.

"Subject" and "patient" are used interchangeably and refer to, except where indicated, mammals such as humans and non-human primates, as well as rabbits, rats, mice, goats, pigs, and other mammalian species.

"Recombinant antibody" refers to all antibodies produced by recombinant techniques. These include antibodies obtained from an animal that is transgenic for the immunoglobulin locus, antibodies expressed from a recombinant expression vector, and antibodies created, prepared, and expressed by splicing of any immunoglobulin gene sequence to any other nucleic acid sequence.

Anti-14-3-3 Antibodies

In one aspect, the invention provides anti-14-3-3 eta antibodies. The anti-14-3-3 eta antibodies of the invention are capable of (i) binding specifically to human 14-3-3 eta protein in its native configuration, as evidenced by, for example, immunoprecipitation, and (ii) binding selectively to human 14-3-3 eta protein over other human 14-3-3 protein isoforms.

By specifically binding to a human 14-3-3 eta protein in its "natural configuration" is meant an ability to bind to 14-3-3 protein as encountered in vivo. This may be evidenced, for example, by the ability of antibody to immunoprecipitate 14-3-3 eta protein from a biological sample.

By "selectivity for said human 14-3-3 eta protein over other human 14-3-3 protein isoforms" is meant an ability to bind specifically to human 14-3-3 eta protein and to bind preferentially to 14-3-3 eta as compared to other human 14-3-3 protein isoforms under the same conditions. Selectivity may be evidenced, for example, using an ELISA assay, which may be done using, for example, supernatant from hybridoma clones. A control (e.g., pre-immune serum) is preferably used. A "selective" antibody is capable of recognizing 14-3-3 eta and generating a higher signal against 14-3-3 eta as compared to other 14-3-3 isoforms, preferably at least a 1.5 fold, more preferably at least a 2 fold higher signal as compared to other isoforms. In a preferred embodiment, a selective antibody has an ability to selectively immunoprecipitate 14-3-3 eta as compared to other 14-3-3 isoforms.

In a preferred embodiment, the anti-14-3-3 eta antibody exhibits selectivity for said human 14-3-3 eta protein over human 14-3-3 alpha, beta, delta, epsilon, gamma, tau, and zeta proteins. This may be evidenced, for example, by ELISA.

In a preferred embodiment, an anti-14-3-3 eta antibody of the invention is capable of binding to 14-3-3 eta protein that is aberrantly localized in the extracellular synovial space in arthritis. This may be evidenced, for example, by Immunoprecipitation of 14-3-3 eta protein present in a synovial fluid sample from a patient having arthritis.

In a preferred embodiment, an anti-14-3-3 eta antibody is capable of inhibiting the induction of MMP by 14-3-3 eta. Preferably, the MMP is selected from the group consisting of MMP-1, 3, 8, 9, 10, 11 and 13, with MMP-1 and MMP-3 being especially preferred. Such capability may be determined by in vitro assay or in vivo assay. As will be appreciated by one of skill in the art, the assays will be designed such that in the absence of anti-14-3-3 eta antibody, the presence of 14-3-3 eta will result in the induction of MMP. An ability to reduce this induction of MMP by 14-3-3 eta can evidence such a function-inhibiting capability for an anti-14-3-3 antibody.

14-3-3 Eta Epitopes

In a preferred embodiment, an anti-14-3-3 eta antibody of the invention does not bind to an epitope at the N-terminus of 14-3-3 eta. By 14-3-3 eta "N-terminus" is meant amino acids 1-12 (i.e., DREQLLQRARLA (SEQ ID NO:33).

In a preferred embodiment, an anti-14-3-3 eta antibody of the invention is capable of binding to an epitope comprising a peptide selected from the group consisting of 14-3-3 eta loop peptides, 14-3-3 eta helix peptides, and 14-3-3 eta non-helix peptides, with eta loop peptides being especially preferred. See Table I herein. Exemplary 14-3-3 eta loop, helix, and non-helix peptides are disclosed in Table 1 herein. Notably, SEQ ID NO:30 varies from corresponding 14-3-3 eta sequence in that a cysteine occurring in 14-3-3 eta sequence has been replaced by serine to avoid disulfide bond formation. In one embodiment, the invention provides antibodies that also bind to the natural 14-3-3 sequence correlate of SEQ ID NO:30 comprising a cysteine. In one embodiment, the invention provides antibodies capable of binding to peptide sequences that vary from those listed in Table 1 by substitution of serine for cysteine.

(i) Loop Peptides

In a preferred embodiment, the 14-3-3 eta loop peptide comprises an amino acid sequence selected from the group consisting of SEQ ID NOs:11-16. In another embodiment, an anti-14-3-3 eta antibody binds to a region of 14-3-3 eta that overlaps with an amino acid sequence corresponding to a sequence selected from the group consisting of SEQ ID NOs:11-16.

In an especially preferred embodiment, an anti-14-3-3 eta antibody of the invention binds to an amino acid sequence selected from the group consisting of LDKFLIKNSNDF (SEQ ID NO:30), KKLEKVKAYR (SEQ ID NO:31), and KNSVVEASEAAYKEA (SEQ ID NO:32).

(ii) Helix Peptides

In a preferred embodiment, the 14-3-3 eta helix peptide comprises an amino acid sequence selected from the group consisting of SEQ ID NOs:1-10. In another embodiment, an anti-14-3-3 eta antibody binds to a region of 14-3-3 eta that overlaps with an amino acid sequence corresponding to a sequence selected from the group consisting of SEQ ID NOs:1-10.

(iii) Non-Helix Peptides

In a preferred embodiment, the 14-3-3 eta non-helix peptide comprises an amino acid sequence selected from the group consisting of SEQ ID NOs:17-32. In another embodiment, an anti-14-3-3 eta antibody binds to a region of 14-3-3 eta that overlaps with an amino acid sequence corresponding to a sequence selected from the group consisting of SEQ ID NOs:17-32.

Monoclonal Antibodies, Hybridomas, and Methods of Making the Same

In one embodiment, the present invention provides anti-14-3-3 eta antibodies that are monoclonal anti-14-3-3 eta antibodies. Also provided are hybridoma cell lines capable of producing such antibodies. Also provided are methods for producing such hybridomas and methods for producing such antibodies.

The monoclonal anti-14-3-3 eta antibodies provided include antibodies that bind to 14-3-3 eta loop, helix, and non-helix peptides described herein.

In one aspect, the invention provides hybridomas produced by fusion of a spleen cell derived from a mouse immunized with an immunogen comprising a 14-3-3 eta loop, helix, or non-helix peptide. Also provided are monoclonal antibodies produced by such hybridomas.

The present invention further provides methods of producing such monoclonal antibodies, or derivatives thereof, comprising cultivating a hybridoma of the invention under suitable conditions, whereby a monoclonal antibody is produced, and obtaining the antibody and/or derivative thereof from the cell and/or from the cell culture medium.

Antibodies can be produced readily by one skilled in the art. The general methodology for making monoclonal antibodies by hybridomas is now well known to the art. See, e.g., M. Schreier et al., Hybridoma Techniques (Cold Spring Harbor Laboratory) 1980; Hammerling et al., Monoclonal Antibodies and T-Cell Hybridomas (Elsevier Biomedical Press) 1981.

In some embodiments, these methods comprise cultivating a hybridoma cell under suitable conditions wherein the antibody is produced, and obtaining the antibody and/or derivative thereof from the cell and/or from the cell culture medium.

The present invention also contemplates the use of phage libraries to pan for antibodies capable of binding to the 14-3-3 peptides of interest described herein. For example, see Konthur et al., Targets, 1:30-36, 2002.

The antibodies produced by any means can be purified by methods known to the skilled artisan. Purification methods include, among others, selective precipitation, liquid chromatography, HPLC, electrophoresis, chromatofocusing, and various affinity techniques. Selective precipitation may use ammonium sulfate, ethanol (Cohn precipitation), polyethylene glycol, or other agents available in the art. Liquid chromatography mediums, include, among others, ion exchange medium DEAF, polyaspartate, hydroxylapatite, size exclusion (e.g., those based on crosslinked agarose, acrylamide, dextran, etc.), hydrophobic matrices (e.g., Blue Sepharose). Affinity techniques typically rely on proteins that interact with the immunoglobulin Fc domain. Protein A from *Staphylococcus aureas* can be used to purify antibodies that are based on human γ1, γ2, or γ4 heavy chains (Lindmark et al., J. Immunol. Meth. 62:1-13 (1983)). Protein G from C and G streptococci is useful for all mouse isotypes and for human γ3 (Guss et al., EMBO J. 5:15671575 (1986)). Protein L, a *Peptostreptococcus magnus* cell-wall protein that binds immunoglobulins (Ig) through k light-chain interactions (BD Bioscience/ClonTech. Palo Alto, Calif.), is useful for affinity purification of Ig subclasses IgM, IgA, IgD, IgG, IgE and IgY. Recombinant forms of these proteins are also commercially available. If the antibody contains metal binding residues, such as phage display antibodies constructed to contain histidine tags, metal affinity chromatography may be used. When sufficient amounts of specific cell populations are available, antigen affinity matrices may be made with the cells to provide an affinity method for purifying the antibodies.

In a preferred embodiment, isolation involves affinity chromatography using 14-3-3 eta or fragment thereof.

The present invention provides the antibodies described herein, as well as corresponding antibody fragments and antigen-binding portions. All are encompassed by the term anti-14-3-3 eta antibody. The terms "antibody fragment" or "antigen-binding portion" of an antibody (or simply "antibody portion") of the present invention, as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antibody fragment" or "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (e.g., Ward et al., (1989) Nature 341:544-546), which consists of a VH domain; and (vi) an isolated complementarity determining region (CDR), and (vii) bispecific single chain Fv dimers (e.g., PCT/US92/09965). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. The antibody fragments may be modified. For example, the molecules may be stabilized by the incorporation of disulphide bridges linking the VH and VL domains (Reiter et al., 1996, Nature Biotech. 14:1239-1245).

Immunoglobulin molecules can be cleaved into fragments. The antigen binding region of the molecule can be divided into either F(ab')2 or Fab fragments. The F(ab')2 fragment is divalent and is useful when the Fc region is either undesirable or not a required feature. The Fab fragment is univalent and is useful when an antibody has a very high avidity for its antigen. Eliminating the Fc region from the antibody decreases non-specific binding between the Fc region and Fc receptor bearing cells. To generate Fab or F(ab')2 fragments, the antibodies are digested with an enzyme. Proteases that cleave at the hinge region of an immunoglobulin molecule preserve the disulfide bond(s) linking the Fab domains such that they remain together following cleavage. A suitable protease for this purpose is pepsin. For producing Fab fragments, proteases are chosen such that cleavage occurs above the hinge region containing the disulfide bonds that join the heavy chains but which leaves intact the disulfide bond linking the heavy and light chain. A suitable protease for making Fab fragments is papain. The fragments are purified by the methods described above, with the exception of affinity techniques requiring the intact Fc region (e.g., Protein A affinity chromatography).

Antibody fragments can be produced by limited proteolysis of antibodies and are called proteolytic antibody fragments. These include, but are not limited to, the following: F(ab')2 fragments, Fab' fragments, Fab'-SH fragments, and Fab fragments. "F(ab')2 fragments" are released from an antibody by limited exposure of the antibody to a proteolytic enzyme, e.g., pepsin or ficin. An F(ab')2 fragment comprises two "arms," each of which comprises a variable region that is directed to and specifically binds a common antigen. The two Fab' molecules are joined by interchain disulfide bonds in the hinge regions of the heavy chains; the Fab' molecules may be directed toward the same (bivalent) or different (bispecific) epitopes. "Fab' fragments" contain a single antigen-binding domain comprising an Fab and an additional portion of the heavy chain through the hinge region. "Fab'-SH fragments" are typically produced from F(ab')2 fragments, which are held together by disulfide bond(s) between the H chains in an F(ab')2 fragment. Treatment with a mild reducing agent such as, by way of non-limiting example, beta-mercaptoethylamine, breaks the disulfide bond(s), and two Fab' fragments are released from one F(ab')2 fragment. Fab'-SH fragments are monovalent and monospecific. "Fab fragments" (i.e., an antibody fragment that contains the antigen-binding domain and comprises a light chain and part of a heavy chain bridged by a disulfide bond) may be produced by papain digestion of intact antibodies. A convenient method is to use papain immobilized on a resin so that the enzyme can be easily removed and the digestion terminated. Fab fragments do not have the disulfide bond(s) between the H chains present in an F(ab')2 fragment.

"Single-chain antibodies" are one type of antibody fragment. The term single chain antibody is often abbreviated as "scFv" or "sFv." These antibody fragments are produced using recombinant DNA technology. A single-chain antibody consists of a polypeptide chain that comprises both a $V_H$ and a $V_L$ domains which interact to form an antigen-binding site. The $V_H$ and $V_L$ domains are usually linked by a peptide of 10 to 25 amino acid residues.

The term "single-chain antibody" further includes but is not limited to a disulfide-linked Fv (dsFv) in which two single-chain antibodies (each of which may be directed to a different epitope) are linked together by a disulfide bond; a bispecific sFv in which two discrete scFvs of different specificity are connected with a peptide linker; a diabody (a dimerized sFv formed when the $V_H$ domain of a first sFv assembles with the $V_L$ domain of a second sFv and the $V_L$ domain of the first sFv assembles with the $V_H$ domain of the second sFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes).

"Complementary determining region peptides" or "CDR peptides" are another form of an antibody fragment. In one embodiment, the invention provides such CDR peptides. In a preferred embodiment, such CDR peptides function as 14-3-3 eta antagonists. A CDR peptide (also known as "minimal recognition unit") is a peptide corresponding to a single complementarity-determining region (CDR), and can be prepared by constructing genes encoding the CDR of an antibody of interest. Such genes are prepared, for example, by using the polymerase chain reaction to synthesize the variable region from RNA of antibody-producing cells. See, for example, Larrick et al., Methods: A Companion to Methods in Enzymology 2:106, 1991.

In "cysteine-modified antibodies," a cysteine amino acid is inserted or substituted on the surface of antibody by genetic manipulation and used to conjugate the antibody to another molecule via, e.g., a disulfide bridge. Cysteine substitutions or insertions for antibodies have been described (see U.S. Pat. No. 5,219,996). Methods for introducing Cys residues into the constant region of the IgG antibodies for use in site-specific conjugation of antibodies are described by Stimmel et al. (J. Biol. Chem 275:330445-30450, 2000).

The present disclosure further provides humanized and non-humanized antibodies. Humanized forms of non-human (e.g., mouse) antibodies are chimeric antibodies that contain minimal sequence derived from non-human immunoglobulin. Generally, humanized antibodies are non-human antibodies that have had the variable-domain framework regions swapped for sequences found in human antibodies. The humanized antibodies may be human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin.

Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239: 1534-1536. Humanized antibodies can also be generated using mice with a genetically engineered immune system. e.g., Roque et al., 2004, Biotechnol. Prog. 20:639-654.

It can be desirable to modify the antibodies of the invention with respect to effector function. For example, cysteine residue(s) can be introduced into the Fc region, thereby allowing interchain disulfide bond formation in this region. Homodimeric antibodies can also be prepared using heterobifunctional cross-linkers, e.g., Wolff et al. Cancer Research, 53:2560-2565 (1993). Alternatively, an antibody can be engineered that has dual Fc regions. See for example Stevenson et al., Anti-Cancer Drug Design, 3:219-230 (1989).

Modified Antibodies

In one embodiment, the invention provides anti-14-3-3 eta antibodies that are modified antibodies. Modified antibodies include recombinant antibodies as described herein.

Numerous types of modified or recombinant antibodies will be appreciated by those of skill in the art. Suitable types of modified or recombinant antibodies include, without limitation, engineered monoclonal antibodies (e.g. chimeric monoclonal antibodies, humanized monoclonal antibodies), domain antibodies (e.g. Fab, Fv, VH, scFV, and dsFv fragments), multivalent or multispecific antibodies (e.g. diabodies, minibodies, miniantibodies, (scFV)2, tribodies, and tetrabodies), and antibody conjugates as described herein.

In one aspect, the present invention provides anti-14-3-3 eta antibodies which are domain antibodies. "Domain antibodies" are functional binding domains of antibodies, corresponding to the variable regions of either the heavy (VH) or light (VL) chains of human antibodies. Domain antibodies may have a molecular weight of approximately 13 kDa, or less than one-tenth the size of a full antibody. They are well expressed in a variety of hosts including bacterial, yeast, and mammalian cell systems. In addition, domain antibodies are highly stable and retain activity even after being subjected to harsh conditions, such as freeze-drying or heat denaturation. See, for example, U.S. Pat. Nos. 6,291, 158; 6,582,915; 6,593,081; 6,172,197; US Serial No. 2004/ 0110941; European Patent 0368684; U.S. Pat. No. 6,696, 245, WO04/058821, WO04/003019 and WO03/002609. In one embodiment, the domain antibody of the present invention is a single domain. Single domain antibodies may be prepared, for example, as described in U.S. Pat. No. 6,248, 516.

In another aspect, the present invention includes multi-specific antibodies. Multi-specific antibodies include bispecific, trispecific, etc. antibodies. Bispecific antibodies can be produced via recombinant means, for example by using leucine zipper moieties (i.e., from the Fos and Jun proteins, which preferentially form heterodimers; e.g., Kostelny et al., 1992, J. Immnol. 148:1547) or other lock and key interactive domain structures, for example as described in U.S. Pat. No. 5,582,996. Additional useful techniques include those described in U.S. Pat. Nos. 5,959,083; and 5,807,706.

Bispecific antibodies are also sometimes referred to as "diabodies." These are antibodies that bind to two (or more) different antigens. Also known in the art are triabodies (a trimerized sFv, formed in a manner similar to a diabody, but in which three antigen-binding domains are created in a single complex; the three antigen binding domains may be directed towards the same or different epitopes) or tetrabodies (four antigen-binding domains created in a single complex where the four antigen binding domains may be directed towards the same or different epitopes). Dia-, tria- and tetrabodies can be manufactured in a variety of ways known in the art (e.g., Holliger and Winter, 1993, Current Opinion Biotechnol. 4:446-449), e.g., prepared chemically or from hybrid hybridomas. In addition, such antibodies and fragments thereof may be constructed by gene fusion (e.g., Tomlinson et. al., 2000, Methods Enzymol. 326:461-479; WO94/13804; Holliger et al., 1993, Proc. Natl. Acad. Sci. U.S.A. 90:6444-6448).

In another embodiment, the present invention provides minibodies, which are minimized antibody-like proteins that include a scFV joined to a CH3 domain, that are derived from an anti-14-3-3 eta antibody. Minibodies can be made as described in the art (e.g., Hu et al., 1996, Cancer Res. 56:3055-3061).

In another embodiment, the present invention provides 14-3-3 eta binding domain-immunoglobulin fusion proteins. In one embodiment, the fusion protein may include a 14-3-3 eta binding domain polypeptide fused to an immunoglobulin hinge region polypeptide, which is fused to an immunoglobulin heavy chain CH2 constant region polypeptide fused to an immunoglobulin heavy chain CH3 constant region polypeptide. Under the present invention, 14-3-3 antibody fusion proteins can be made by methods appreciated by those of skill in the art (See for example published U.S. Patent Application Nos. 20050238646, 20050202534, 20050202028, 2005020023, 2005020212, 200501866216, 20050180970, and 20050175614).

In another embodiment, the present invention provides a heavy-chain protein derived from a an anti-14-3-3 eta antibody. Naturally-occurring heavy chain antibodies (e.g. camelidae antibodies having no light chains) have been utilized to develop antibody-derived therapeutic proteins that typically retain the structure and functional properties of naturally-occurring heavy-chain antibodies. They are known in the art as Nanobodies. Heavy chain proteins derived from an anti-14-3-3 eta heavy chain antibody may be made by methods appreciated by those of skill in the art (See for example published U.S. Patent Application Nos. 20060246477, 20060211088, 20060149041, 20060115470, and 20050214857). Further, regarding the production of heavy chain-only antibodies in light chain-deficient mice, see for example Zou et al., JEM, 204:3271-3283, 2007.

In one embodiment, the invention provides modified anti-14-3-3 eta antibodies that are human antibodies. In one embodiment, fully human 14-3-3 antibodies are provided. "Fully human antibody" or "complete human antibody" refers to a human antibody having only the gene sequence of an antibody derived from a human chromosome. The anti-14-3-3 complete human antibody can be obtained by a method using a human antibody-producing mouse having a human chromosome fragment containing the genes for a heavy chain and light chain of a human antibody [see for example Tomizuka, K. et al., Nature Genetics, 16, p. 133-143, 1997; Kuroiwa, Y. et al., Nuc. Acids Res., 26, p. 3447-3448, 1998; Yoshida, H. et al., Animal Cell Technology: Basic and Applied Aspects vol. 10, p. 69-73 (Kitagawa, Y., Matuda, T. and Iijima, S. eds.), Kluwer Academic Publishers, 1999; Tomizuka, K. et al., Proc. Natl. Acad. Sci. USA, 97, 722-727, 2000] or obtained by a method for obtaining a human antibody derived from a phage display selected from a human antibody library (see for example Wormstone, I. M. et al., Investigative Ophthalmology & Visual Science. 43(7), p. 2301-8, 2002; Carmen, S. et al., Briefings in Functional Genomics and Proteomics, 1 (2), p. 189-203, 2002; Siriwardena, D. et al., Ophthalmology, 109 (3), p. 427-431, 2002).

In one aspect, the present invention provides a 14-3-3 antibody that is an antibody analog, sometimes referred to as "synthetic antibodies." For example, alternative protein scaffolds or artificial scaffolds with grafted CDRs may be used. Such scaffolds include, but are not limited to, synthetic scaffolds consisting, for example, of biocompatible polymers. See, for example, Korndorfer et al., 2003, Proteins: Structure, Function, and Bioinformatics, Volume 53, Issue 1:121-129. Roque et al., 2004, Biotechnol. Prog. 20:639-654. In addition, peptide antibody mimetics ("PAMs") can be used, as well as antibody mimetics utilizing fibronectin components as a scaffold.

In one embodiment, the present invention provides cross-linked antibodies that include two or more antibodies described herein attached to each other to form antibody complexes. Cross-linked antibodies are also referred to as antibody multimers, homoconjugates, and heteroconjugates.

In some embodiments, the antibody complexes provided herein include multimeric forms of anti-14-3-3 antibodies. For example, antibody complexes of the invention may take the form of antibody dimers, trimers, or higher-order multimers of monomeric immunoglobulin molecules. Cross-linking of antibodies can be done through various methods know in the art. For example, crosslinking of antibodies may be accomplished through natural aggregation of antibodies, through chemical or recombinant linking techniques or other methods known in the art. For example, purified antibody preparations can spontaneously form protein aggregates containing antibody homodimers, and other higher-order antibody multimers.

In one embodiment, the present invention provides homodimerized antibodies that specifically bind to 14-3-3 eta.

Antibodies can be cross-linked or dimerized through linkage techniques known in the art. Non-covalent methods of attachment may be utilized. In a specific embodiment, crosslinking of antibodies can be achieved through the use of a secondary crosslinker antibody. The crosslinker antibody can be derived from a different animal compared to the antibody of interest. For example, a goat anti-mouse antibody (Fab specific) may be added to a mouse monoclonal antibody to form a heterodimer. This bivalent crosslinker antibody recognizes the Fab or Fc region of the two antibodies of interest forming a homodimer.

In one embodiment of the present invention, an antibody that specifically binds to 14-3-3 antigen is cross-linked using a goat anti-mouse antibody (GAM). In another embodiment, the GAM crosslinker recognizes the Fab or Fc region of two antibodies, each of which specifically binds 14-3-3 eta.

Methods for covalent or chemical attachment of antibodies may also be utilized. Chemical crosslinkers can be homo or heterobifunctional and will covalently bind with two antibodies forming a homodimer. Cross-linking agents are well known in the art; for example, homo- or heterobifunctional linkers as are well known (see the 2006 Pierce Chemical Company Crosslinking Reagents Technical Handbook; Hermanson, G. T., Bioconjugate Techniques, Academic Press, San Diego, Calif. (1996); Aslam M. and Dent A H., Bioconjugation: protein coupling techniques for the biomedical sciences, Houndsmills, England: Macmillan Publishers (1999); Pierce: Applications Handbook & Catalog, Perbio Science, Ermbodegem, Belgium (2003-2004); Haughland, R. P., Handbook of Fluorescent Probes and Research Chemicals Eugene, 9th Ed., Molecular Probes, OR (2003); and U.S. Pat. No. 5,747,641) Those of skill in the art will appreciate the suitability of various functional groups on the amino acid(s) of an antibody for modification, including cross-linking. Suitable examples of chemical cross-linkers used for antibody crosslinking include, but not limited to, SMCC [succinimidyl 4-(maleimidomethyl)cyclohexane-1-carboxylate], SATA [N-succinimidyl S-acethyl-thio-acetate], hemi-succinate esters of N-hydroxysuccinimide; sulfo-N-hydroxy-succinimide; hydroxybenzotriazole, and p-nitrophenol; dicyclohexylcarbodiimide (DCC), 1-(3-dimethylaminopropyl)-3-ethylcarbodiimide (ECD), and 1-(3-dimethylaminopropyl)-3-ethylcarbodiimide methiodide (EDCI) (see, e.g., U.S. Pat. No. 4,526,714, the disclosure of which is fully incorporated by reference herein). Other linking reagents include glutathione, 3-(diethoxy-phosphoryloxy)-1,2,3-benzotriazin-4(3H)-one (DEPBT), onium salt-based coupling reagents, polyoxyethylene-based heterobifunctional cross-linking reagents, and other reagents (Haitao, et al., Organ Lett 1:91-94 (1999); Albericio et al., J Organic Chemistry 63:9678-9683 (1998); Arpicco et al., Bioconjugate Chem. 8:327-337 (1997); Frisch et al., Bioconjugate Chem. 7:180-186 (1996); Deguchi et al., Bioconjugate Chem. 10:32-37 (1998); Beyer et al., J. Med. Chem. 41:2701-2708 (1998); Drouillat et al., J. Pharm. Sci. 87:25-30 (1998); Trimble et al., Bioconjugate Chem. 8:416-423 (1997)). An exemplary protocols for the formation of antibody homodimers is given in U.S. Patent Publication 20060062786. Techniques for conjugating therapeutic compounds to antibodies are also described in Arnon et al., "Monoclonal Antibodies for Immunotargeting of Drugs in Cancers Therapy," in Monoclonal Antibodies and Cancer Therapy, Reisfeld et al., ed., pp 243-256, Alan R. Liss, Inc. (1985); Thorpe, et al. "The Preparation and Cytotoxic Properties of Antibody Toxin Conjugates," Immunol. Rev. 62:119-58 (1982); and Pietersz, G. A., "The linkage of cytotoxic drugs to monoclonal antibodies for the treatment of cancer," Bioconjugate Chemistry 1(2):89-95 (1990), all references incorporated herein by reference.

In addition, the antibody-antibody conjugates of this invention can be covalently bound to each other by techniques known in the art such as the use of the heterobifunctional cross-linking reagents, GMBS (maleimidobutryloxy succinimide), and SPDP (N-succinimidyl 3-(2-pyridyldi-thio)propionate) [see, e.g., Hardy, "Purification And Coupling Of Fluorescent Proteins For Use In Flow Cytometry", Handbook Of Experimental Immunology, Volume 1, Immunochemistry, Weir et al. (eds.), pp. 31.4-31.12 4th Ed., (1986), and Ledbetter et al. U.S. Pat. No. 6,010,902].

In addition, antibodies may be linked via a thioether cross-link as described in U.S. Patent Publication 20060216284, U.S. Pat. No. 6,368,596. As will be appreciated by those skilled in the art, antibodies can be crosslinked at the Fab region. In some embodiments, it is desirable that the chemical crosslinker not interact with the antigen-binding region of the antibody as this may affect antibody function.

Conjugated Antibodies

The anti-14-3-3 eta antibodies disclosed herein include antibodies conjugated to inorganic or organic compounds, including, by way of example and not limitation, other proteins, nucleic acids, carbohydrates, steroids, and lipids (see for example Green, et al., Cancer Treatment Reviews, 26:269-286 (2000). The compound may be bioactive. Bioactive refers to a compound having a physiological effect on the cell as compared to a cell not exposed to the compound. A physiological effect is a change in a biological process, including, by way of example and not limitation, DNA replication and repair, recombination, transcription, translation, secretion, membrane turnover, cell adhesion, signal transduction, cell death, and the like. A bioactive compound includes pharmaceutical compounds. In one embodiment, an anti-14-3-3 eta antibody is conjugated to a 14-3-3 antagonist peptide, preferably R-18, preferably via a linker. Regarding R18, see, for example, (Wang et al. 1999—REF 35)

Pharmaceutical Compositions, Administration, and Dosages

The anti-14-3-3 eta antibodies of the invention can be incorporated into pharmaceutical compositions suitable for administration to a subject. Typically, the pharmaceutical composition comprises an anti-14-3-3 eta antibody of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable substances such as wetting or minor amounts of auxiliary substances such as wetting or emulsifying agents, preservatives or buffers, which enhance the shelf life or effectiveness of the anti-14-3-3 eta antibody.

In a preferred embodiment, the anti-14-3-3 eta antibodies are targeted to 14-3-3 eta protein that is localized extracellularly. Accordingly, such therapeutic compositions are formulated and administration is such that the anti-14-3-3 eta antibody so delivered is available to engage extracellular 14-3-3 eta protein.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular, with intracapsular being especially preferred). In one embodiment, the anti-14-3-3 eta antibody is administered by intravenous infusion or injection. In another preferred embodiment, the anti-14-3-3 eta antibody is administered by intramuscular or subcutaneous injection. In a preferred embodiment, direct injection into the synovium is done.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The anti-14-3-3 eta antibodies of the present invention can be administered by a variety of methods known in the art, including intravenous injection or infusion. Direct administration to the synovium is one preferred route of administration. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978. Representative formulation technology is taught in, inter alia, Remington: The Science and Practice of Pharmacy, 19th Ed., Mack Publishing Co., Easton, Pa. (1995) and Handbook of Pharmaceutical Excipients, 3rd Ed, Kibbe, A. H. ed., Washington D.C., American Pharmaceutical Association (2000)

In certain embodiments, an anti-14-3-3 eta antibody of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an anti-14-3-3 eta antibody of the invention is coformulated with and/or coadministered with one or more additional therapeutic agents. For example, a DMARD or DMOAD or another antibody. Such combination therapies may advantageously utilize lower dosages of the administered therapeutic agents, thus avoiding possible toxicities or complications associated with the various monotherapies.

The pharmaceutical compositions of the invention may include a "therapeutically effective amount" or a "prophylactically effective amount" of an antibody of the invention. A "therapeutically effective amount" refers to an amount effective, at dosages and for periods of time necessary, to achieve the desired therapeutic result. A therapeutically effective amount of the anti-14-3-3 eta antibody may vary according to factors such as the disease state, age, sex, and weight of the individual, and the ability of the anti-14-3-3 eta antibody to elicit a desired response in the individual. A therapeutically effective amount is also one in which any toxic or detrimental effects of the antibody are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles, as indicated above. Alternatively, a pharmaceutical composition may be stored in a freeze-dried condition requiring only the addition of a sterile liquid carrier immediately prior to use.

Therapeutic Use of Anti-14-3-3 Eta Antibodies

By "treatment" herein is meant therapeutic or prophylactic treatment, or a suppressive measure for the disease, disorder or undesirable condition. Treatment encompasses administration of the subject anti-14-3-3 eta antibodies in an appropriate form prior to the onset of disease symptoms and/or after clinical manifestations, or other manifestations, of the disease to reduce disease severity, halt disease progression, or eliminate the disease. Prevention of the disease includes prolonging or delaying the onset of symptoms of the disorder or disease, preferably in a subject with increased susceptibility to the disease.

In one aspect, the invention provides methods of treating diseases that involve 14-3-3 eta. The methods comprise administering a therapeutically effective amount of an anti-14-3-3 eta antibody of the invention to a patient. In some embodiments, the methods comprise combination treatments.

In one embodiment, the invention provides methods of treating arthritis, including methods of treating ankylosing spondylitis, Behçet's Disease, diffuse idiopathic skeletal hyperostosis (DISH), Ehlers-Danlos Syndrome (EDS), Felty's Syndrome, fibromyalgia, gout, infectious arthritis, juvenile arthritis, lupus, mixed connective tissue disease (MCTD), osteoarthritis, Paget's Disease, polymyalgia rheumatica, polymyositis and dermatomyositis, pseudogout, psoriatic arthritis, Raynaud's Phenomenon, reactive arthritis, rheumatoid arthritis, scleroderma, Sjögren's Syndrome, Still's Disease, and Wegener's granulomatosis.

In one embodiment, the method involves a combination treatment, wherein at least one other therapeutic agent is administered in addition to one or more anti-14-3-3 eta antibodies of the invention. In a preferred embodiment, the therapeutic agent is selected from the group consisting of disease-modifying antirheumatic drugs (DMARDs), disease modifying osteoarthritis drugs (DMOADs; for example, see Loeser, Reumatologia, 21:104-106, 2005), anti-TNFα antibody, anti-IL-1 antibody, anti-CD4 antibody, anti-CTLA4 antibody, anti-CD20 antibody, anti-IL-6 antibody, leflunomide, sulfasalazine, and methotrexate.

Diagnostic, Prognostic and Theragnostic Methods, and Treatment Monitoring

In one aspect, the invention provides methods for diagnosing diseases and conditions that involve 14-3-3 eta. The methods comprise using an anti-14-3-3 eta antibody of the invention to detect an alteration in 14-3-3 eta protein, e.g., a change in expression, localization, function, etc. In one embodiment, detection involves immunoprecipitation with an anti-14-3-3 eta antibody of the invention. In one embodiment, detection involves the use of ELISA employing an anti-14-3-3 eta antibody of the invention. In one embodiment, detection involves Western blotting using an anti-14-3-3 eta antibody of the invention. In one embodiment, detection involves the use of an anti-14-3-3 eta antibody of the invention in immunohistochemistry. In one embodiment, detection involves the use of an anti-14-3-3 eta antibody of the invention in immunofluorescence. In one embodiment, detection involves the use of an anti-14-3-3 eta antibody of the invention in FACS analysis. In one embodiment, detection involves the use of an anti-14-3-3 eta antibody of the invention in radioimmunoassay. In one embodiment, detection involves the use of an anti-14-3-3 eta antibody of the invention in a strip test. In one embodiment, detection involves the use of an anti-14-3-3 eta antibody of the invention in a point of care test. In one embodiment, detection of 14-3-3 eta is combined with detection of another marker of the condition (e.g., MMP, anti-CCP, anti-RF and/or CRP for arthritis).

In one embodiment, the invention provides methods for diagnosing inflammatory conditions. In a preferred embodiment, methods for diagnosing arthritis are provided. Included are methods for diagnosing a disease selected from the group consisting of ankylosing spondylitis, Behçet's Disease, diffuse idiopathic skeletal hyperostosis (DISH), Ehlers-Danlos Syndrome (EDS), Felty's Syndrome, fibromyalgia, gout, infectious arthritis, juvenile arthritis, lupus, mixed connective tissue disease (MCTD), osteoarthritis, Paget's Disease, polymyalgia rheumatica, polymyositis and dermatomyositis, pseudogout, psoriatic arthritis, Raynaud's Phenomenon, reactive arthritis, rheumatoid arthritis, scleroderma, Sjögren's Syndrome, Still's Disease, and Wegener's granulomatosis.

In general, arthritis may be detected in a patient based on the presence 14-3-3 eta in the synovial fluid, plasma, or serum of a patient. In other words, extracellular 14-3-3 eta protein may be used as a marker to indicate arthritis.

In addition, the presence of 14-3-3 eta, or the relative levels of isoforms of 14-3-3 proteins including 14-3-3 eta, as determined through the use of an anti-14-3-3 eta antibody of the invention and other anti-14-3-3 antibodies may be a prognostic indicator of early-stage arthritis, before it progresses to a debilitating form. An advantage of early prognosis or diagnosis is earlier implementation of a treatment regimen.

The presence or relative levels of 14-3-3 eta may correlate with the presence or relative levels of other proteins in the patient sample, for example matrix metalloproteinases (MMPs), such as MMP-1 or MMP-3. At least 25 different MMPs have been identified. Detection of 14-3-3 eta in combination with at least one MMP in a patient sample may be used to diagnose arthritis. Additionally, the presence or relative levels of 14-3-3 eta in combination with at least one MMP in a patient sample may be used as a prognostic indicator of early-stage arthritis, before the arthritis progresses to a debilitating form.

In one embodiment, the methods involve detecting 14-3-3 eta protein in the synovial fluid, plasma, or serum of a patient. In one embodiment, detection is done by immunoprecipitation of 14-3-3 eta protein from synovial fluid, plasma, or serum using an anti-14-3-3 eta antibody of the invention. In one embodiment, detection involves the use of ELISA employing an anti-14-3-3 eta antibody of the invention. In one embodiment, detection involves Western blotting of a sample comprising synovial fluid, plasma, or serum from a patient using an anti-14-3-3 eta antibody of the invention. In one embodiment, detection involves the use of radioimmunoassay. In one embodiment, detection involves the use of a strip test. In one embodiment, detection involves the use of a point of care test. In one embodiment, detection of 14-3-3 eta is combined with detection of another marker of arthritis (e.g., MMP, anti-CCP, anti-RF and/or CRP).

In one embodiment the invention provides methods for diagnosing neurological conditions. In a preferred embodiment, methods for diagnosing a disease selected from the group consisting of bacterial meningitis and Creutzfeldt Jakob disease are provided. In one embodiment, the presence of 14-3-3 eta in cerebrospinal fluid is detected.

In one aspect, the invention provides methods for determining the response potential of a patient to treatment directed at an inflammatory condition. In a preferred embodiment, methods for determining the response potential of a patient to treatment directed at arthritis are provided. Included are methods for determining the response potential to treatment of a disease selected from the group consisting of ankylosing spondylitis, Behçet's Disease, diffuse idiopathic skeletal hyperostosis (DISH), Ehlers-Danlos Syndrome (EDS), Felty's Syndrome, fibromyalgia, gout, infectious arthritis, juvenile arthritis, lupus, mixed connective tissue disease (MCTD), osteoarthritis, Paget's Disease, polymyalgia rheumatica, polymyositis and dermatomyositis, pseudogout, psoriatic arthritis, Raynaud's Phenomenon, reactive arthritis, rheumatoid arthritis, scleroderma, Sjögren's Syndrome, Still's Disease, and Wegener's granulomatosis.

In one embodiment, the methods involve determining the level of 14-3-3 eta in a patient sample using an anti-14-3-3 eta antibody of the invention. In a preferred embodiment, the level of 14-3-3 eta in the patient sample is compared to that of samples from subjects whose ability to respond to treatment is known. A relatively high level of 14-3-3 eta in a first patient sample as compared to a sample from a non-inflammatory subject and/or a sample from another inflammatory patient may indicate the first patient is a preferred candidate for treatment with anti-14-3-3 eta antibody or an alternate DMARD therapy such as anti-TNF. Conversely, a relatively low level of 14-3-3 eta in a first patient sample as compared to a sample from another inflammatory patient may indicate the first patient is not a preferred candidate for treatment with anti-14-3-3 eta antibody or an alternate DMARD therapy such as anti-TNF, especially if the level is closer to that of a sample from a non-inflammatory subject.

In one aspect, the invention provides methods for distinguishing between subtypes of inflammatory disorders. In a preferred embodiment methods for distinguishing between subtypes of arthritis are provided. In one embodiment, the methods involve determining the level of 14-3-3 eta in a patient sample using an anti-14-3-3 eta antibody of the invention. In a preferred embodiment, the level of 14-3-3 eta in the patient is compared to that of samples from subjects whose subtype of inflammatory disorder or prognosis is known.

In one aspect, the invention provides prophylactic methods for preventing the development of conditions involving 14-3-3 eta.

In one embodiment, the invention provides prophylactic methods for preventing the development of an inflammatory condition in a subject at risk of developing an inflammatory condition. In a preferred embodiment, prophylactic methods for preventing arthritis in a subject at risk of developing arthritis are provided. Included are prophylactic methods for preventing a disease selected from the group consisting of ankylosing spondylitis, Behçet's Disease, diffuse idiopathic skeletal hyperostosis (DISH), Ehlers-Danlos Syndrome (EDS), Felty's Syndrome, fibromyalgia, gout, infectious arthritis, juvenile arthritis, lupus, mixed connective tissue disease (MCTD), osteoarthritis, Paget's Disease, polymyalgia rheumatica, polymyositis and dermatomyositis, pseudogout, psoriatic arthritis, Raynaud's Phenomenon, reactive arthritis, rheumatoid arthritis, scleroderma, Sjögren's Syndrome, Still's Disease, and Wegener's granulomatosis. The methods comprise administering to the subject an anti-14-3-3 eta antibody of the invention. In one embodiment the anti-14-3-3 eta antibody is administered as a component of a combination therapy described herein.

In one aspect, the invention provides methods for monitoring treatment of an inflammatory condition. In a preferred embodiment, methods for monitoring the treatment of arthritis are provided. Included are methods for monitoring the treatment of a disease selected from the group consisting of ankylosing spondylitis, Behçet's Disease, diffuse idiopathic skeletal hyperostosis (DISH), Ehlers-Danlos Syndrome (EDS), Felty's Syndrome, fibromyalgia, gout, infectious arthritis, juvenile arthritis, lupus, mixed connective tissue disease (MCTD), osteoarthritis, Paget's Disease, polymyalgia rheumatica, polymyositis and dermatomyositis, pseudogout, psoriatic arthritis, Raynaud's Phenomenon, reactive arthritis, rheumatoid arthritis, scleroderma, Sjögren's Syndrome, Still's Disease, and Wegener's granulomatosis.

In one embodiment, the methods involve determining the level of 14-3-3 eta in patient samples using an anti-14-3-3 eta antibody of the invention and monitoring the level of 14-3-3 eta in a patient undergoing treatment.

In one aspect the invention provides kits for detecting the presence of 14-3-3 eta and optionally other markers, e.g., MMPs, in a patient sample, the kit being useful for providing a diagnostic or prognostic result suitable for diagnosing or differentiating various types of diseases involving 14-3-3 eta. A kit comprises an anti-14-3-3 eta antibody of the invention. Such a kit may further include detection reagents specific for particular MMPs that are markers of arthritis. The kit may further include other reagents necessary for the detection of 14-3-3 eta immunologically, such as labeled secondary antibodies, chromogenic or fluorogenic reagents, polymerization agents and/or instructions for using the kit for diagnostic or prognostic purposes.

Regarding diagnostic methods, see also WO 2007/128132 filed 9 May 2007.

There are a variety of assay formats known to those of ordinary skill in the art for using an antibody to detect protein markers in a sample. See, e.g., Harlow and Lane, Antibodies: A Laboratory Manual, Cold Spring Harbor Laboratory, 1988. In general, the presence or absence of arthritis or other condition involving 14-3-3 eta, or patient prognosis, may be determined by (a) contacting a biological sample obtained from a patient with an anti-14-3-3 eta antibody of the invention; (b) detecting in the sample a level of 14-3-3 eta that binds to the antibody; and (c) comparing the level of polypeptide with a predetermined cut-off value (i.e., control).

In a preferred embodiment, the assay involves the use of an anti-14-3-3 eta antibody of the invention immobilized on a solid support to bind to and remove the 14-3-3 eta protein from the remainder of the sample. The bound 14-3-3 eta protein may then be detected using a detection reagent that contains a reporter group and specifically binds to the antibody/protein complex. Such detection reagents may comprise, for example, a binding agent that specifically binds to the 14-3-3 protein. Alternatively, a competitive assay may be utilized, in which a 14-3-3 eta protein is labeled with a reporter group and allowed to bind to the immobilized antibody after incubation of the antibody with the sample. The extent to which components of the sample inhibit the binding of the labeled 14-3-3 eta protein to the antibody is indicative of the reactivity of the sample with the immobilized antibody. Suitable proteins for use within such assays include full length 14-3-3 eta proteins and polypeptide portions thereof to which the antibody binds.

The solid support may be any material known to those of ordinary skill in the art. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The antibody may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antibody and functional groups on the support or may be a linkage by way of a cross-linking agent). Immobilization by adsorption to a well in a microtiter plate or to a membrane is preferred. In such cases, adsorption may be achieved by contacting the antibody, in a suitable buffer, with the solid support for a suitable amount of time. The contact time varies with temperature, but is typically between about 1 hour and about 1 day. In one embodiment, a microtitre plate coated with streptavidin is used in conjunction with a biotinylated antibody.

Covalent attachment of antibody to a solid support may generally be achieved by first reacting the support with a bifunctional reagent that will react with both the support and the antibody.

In certain embodiments, the assay is a two-antibody sandwich assay. This assay may be performed by first contacting an antibody that has been immobilized on a solid support, commonly the well of a microtiter plate, with the sample, such that 14-3-3 eta proteins within the sample are allowed to bind to the immobilized antibody. Unbound sample is then removed from the immobilized protein-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

The immobilized and detection antibodies are preferably different. In a preferred embodiment, the immobilized antibody is an anti-14-3-3 eta antibody of the invention, and the detection antibody is another anti-14-3-3 eta antibody of the invention or another anti-14-3-3 antibody capable of binding to 14-3-3 eta. In one embodiment, the detection antibody is a pan 14-3-3 antibody.

In another embodiment, the detection antibody is an anti-14-3-3 eta antibody of the invention, and the immobilized antibody is another anti-14-3-3 eta antibody of the invention or another anti-14-3-3 antibody capable of binding to 14-3-3 eta. In one embodiment, the immobilized antibody is a pan 14-3-3 antibody.

The methods comprise use of an anti-14-3-3 eta antibody of the invention. As an alternative to the second antibody, another ligand that binds to 14-3-3 eta may be used in conjunction with the anti-14-3-3 eta antibody of the invention. An example of such a ligand is R18. (Wang et al. 1999—REF 35)

Once the antibody is immobilized on the support as described above, the remaining protein binding sites on the support are typically blocked. Any suitable blocking agent known to those of ordinary skill in the art, such as bovine serum albumin or skim milk powder. The immobilized antibody is then incubated with the sample, and 14-3-3 eta protein is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of 14-3-3 eta protein within a sample obtained from an individual with arthritis or other condition involving 14-3-3 eta. Preferably, the contact time is sufficient to achieve a level of binding that is at least about 95% of that achieved at equilibrium between bound and unbound 14-3-3 eta protein. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Reporter groups appropriate to the present methods are well known in the art.

The detection reagent is then incubated with the immobilized antibody-protein complex for an amount of time sufficient to detect the bound 14-3-3 eta protein. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of arthritis, or other condition involving 14-3-3 eta, the signal detected from the reporter group that remains bound to the solid support is generally compared to a signal that corresponds to a predetermined cut-off value (control). In one preferred embodiment, the cut-off value is the average mean signal obtained when the immobilized antibody is incubated with samples from patients without arthritis, or other condition involving 14-3-3 eta. In general, a sample generating a signal that is three standard deviations above the predetermined cut-off value is considered positive for arthritis, or other condition involving 14-3-3 eta. In an alternate preferred embodiment, the cut-off value may be determined using a Receiver Operator Curve, for example see the method of Sackett et al., Clinical Epidemiology: A Basic Science for Clinical Medicine, Little Brown and Co., 1985, p. 106-7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for arthritis, or other condition involving 14-3-3 eta.

In one embodiment, the assay is provided as a point of care assay. For example, in a related embodiment, the assay is performed in a flow-through or strip test format, wherein the antibody is immobilized on a membrane, such as nitrocellulose. In the flow-through test, 14-3-3 proteins within the sample bind to the immobilized antibody as the sample contacts the membrane. A second, labeled binding agent then binds to the binding agent-polypeptide complex as a solution containing the second binding agent contacts the membrane. The detection of bound second binding agent may then be performed as described above. In the strip test format, one end of the membrane to which antibody is bound is immersed in a solution containing the sample. The sample migrates along the membrane through a region containing second 14-3-3 eta binding agent and to the area of immobilized antibody. Concentration of second binding agent at the area of immobilized antibody indicates the presence of arthritis, or other condition involving 14-3-3 eta, or patient prognosis, etc. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Such tests can typically be performed with a very small amount of biological sample and at the point of care.

In a preferred embodiment, the immobilized antibody is an anti-14-3-3 eta antibody of the invention. The second binding agent is another 14-3-3 eta ligand that may or may not bind selectively to 14-3-3 eta protein.

In another embodiment, the second binding agent is an anti-14-3-3 eta antibody of the invention, most preferably an antigen-binding fragment thereof, and the immobilized antibody is an anti-14-3-3 antibody capable of binding to 14-3-3-eta protein. The antibody may or may not bind selectively to 14-3-3 eta protein.

Of course, numerous other assay protocols exist that are suitable for use with the anti-14-3-3 antibodies of the present invention. The above descriptions are intended to be exemplary only.

To improve sensitivity, multiple markers may be assayed within a given sample. In particular, one or more other markers of arthritis, or other condition involving 14-3-3 eta, or prognostic indicators, etc., may be assayed in combination with 14-3-3 protein. These other markers may be proteins or nucleic acids. In a preferred embodiment, wherein the disease is arthritis, one or more of the other markers are MMP proteins or nucleic acids or other factors which are commonly used as indicators for arthritis, e.g., anti-CCP, anti-RF, CRP, etc. Methods for isolating and assaying nucleic acids based on reference sequences are well known in the art.

Combination assays may be done concurrently or sequentially. The selection of markers may be based on routine experiments to determine combinations that results in optimal sensitivity.

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal anti-14-3-3 eta antibody of the invention. Such antibodies may be provided attached to a support material, as described above. One or more additional containers may enclose elements, such as reagents or buffers, to be used in the assay. Such kits may also contain a detection reagent as described above that contains a reporter group suitable for direct or indirect detection of antibody binding.

A kit may also include reagents for detecting additional markers of arthritis, including particular mRNAs encoding particular MMPs.

EXPERIMENTAL

TABLE 1

| 14-3-3 Eta epitopes | | | |
|---|---|---|---|
| SEQ ID NO: 1 | 93-107 | helix | LETVCNDVLSLLDKF |
| SEQ ID NO: 2 | 191-199 | helix | EQACLLAKQ |
| SEQ ID NO: 3 | 144-155 | helix | NSVVEASEAAYK |
| SEQ ID NO: 4 | 144-152 | helix | NSVVEASEA |
| SEQ ID NO: 5 | 147-155 | helix | VEASEAAYK |
| SEQ ID NO: 6 | 163-170 | helix | EQMQPTHP |
| SEQ ID NO: 7 | 168-177 | helix | THPIRLGLAL |
| SEQ ID NO: 8 | 82-92 | helix | VKAYTEKIEKE |
| SEQ ID NO: 9 | 68-79 | helix | QKTMADGNEKKL |
| SEQ ID NO: 10 | 138-146 | helix | ASGEKKNSV |
| SEQ ID NO: 11 | 69-77 | loop | KTMADGNEK |
| SEQ ID NO: 12 | 32-40 | loop | ELNEPLSNE |
| SEQ ID NO: 13 | 103-117 | loop | LLDKFLIKNCNDFQY |
| SEQ ID NO: 14 | 130-143 | loop | YYRYLAEVASGEKK |
| SEQ ID NO: 15 | 184-194 | loop | YEIQNAPEQAC |
| SEQ ID NO: 16 | 206-218 | loop | AELDTLNEDSYKD |
| SEQ ID NO: 17 | 44-57 | non-helix | LLSVAYKNVVGARR |
| SEQ ID NO: 18 | 15-23 | non-helix | EQAERYDDM |
| SEQ ID NO: 19 | 130-138 | non-helix | YYRYLAEVA |
| SEQ ID NO: 20 | 118-125 | non-helix | ESKVFYLK |
| SEQ ID NO: 21 | 210-218 | non-helix | TLNEDSYKD |
| SEQ ID NO: 22 | 77-84 | non-helix | KKLEKVKA |
| SEQ ID NO: 23 | 76-86 | non-helix | EKKLRKVKAYR |
| SEQ ID NO: 24 | 142-158 | non-helix | KKNSVVEASEAAYKEAF |
| SEQ ID NO: 25 | 105-120 | non-helix | DKFLIKNCNDFQYESK |
| SEQ ID NO: 26 | 237-246 | non-helix | QQDEEAGEGN |
| SEQ ID NO: 27 | 75-82 | non-helix | NEKKLEKVK |
| SEQ ID NO: 28 | 104-116 | non-helix | LDKFLIKNCNDFQ |
| SEQ ID NO: 29 | 141-146 | non-helix | EKKNSV |
| SEQ ID NO: 30 | 104-115 | non-helix | LDKFLIKNS*NDF |
| SEQ ID NO: 31 | 77-86 | non-helix | KKLEKVKAYR |
| SEQ ID NO: 32 | 143-157 | non-helix | KNSVVEASEAAYKEA |
| SEQ ID NO: 33 | 1-12 | non-helix | DREQLLQRARLA |

*The internal cysteine amino acid was replaced by the amino acid serine to prevent formation of disulfide bonds.

TABLE 2

Protein Sequence of recombinant human 14-3-3 eta
(SEQ ID NO: 35)

| | | | | | |
|---|---|---|---|---|---|
| SEQ ID NO: 35 | MGDREQLLQR | ARLAEQAERY | DDMASAMKAV | TELNEPLSNE | 40 |
| | DRNLLSVAYK | NVVGARSSW | RVISSIEQKT | MADGNEKKLE | 80 |
| | KVKAYREKIE | KELETVCNDV | LSLLDKFLIK | NCNDFQYESK | 120 |
| | VFYLKMKGDY | YRYLAEVASG | EKKNSVVEAS | EAAYKEAFEI | 160 |
| | SKEQMQPTHP | IRLGLALNFS | VFYYEIQNAP | EQACLLAKQA | 200 |
| | FDDAIAELDT | LNEDSYKDST | LIMQLLRDNL | TLWTSDQQDE | 240 |
| | EAGEGN | | | | |

In sequences comprising a cysteine residue, in one embodiment, the cysteine residue is replaced by a serine residue to avoid the formation of disulfide bonds. The cysteine may be an internal cysteine residue or a terminal cysteine residue.

Peptide epitopes may be modified for various purposes, including conjugation to an additional moiety, e.g., conjugation to a moiety to produce an immunogen comprising the epitope. As will be appreciated, cysteine may be placed appropriately for conjugation to carrier and to provide for exposure of the area that is desired to be exposed for purposes of making antibody. In case of KKLE (SEQ ID NO: 45) the cysteine was added on to the C-terminal end in order to expose the other side. The carrier used may be quite large and may mask the first few amino acids.

Example 1

14-3-3 Eta Immunogen Sequences and Anti-14-3-3 Eta Antibodies

To prepare monospecific anti-14-3-3 eta antibodies, various peptides, 8 to 15 amino acids in length, were selected based on our own criteria. These peptides, as well as full-length recombinant native (untagged) 14-3-3 eta were used as immunogens in the production of monoclonal antibodies. A protein sequence alignment for the 7 isoforms of 14-3-3 is shown in FIG. 4.

Immunogen #1: C-LDKFLIKNSNDF (SEQ ID NO: 41) (Amino Acid Sequence 104-115; "AUG1-CLDK" ('CLDK' disclosed as SEQ ID NO: 44)). A peptide corresponding to a segment of human 14-3-3 eta residues 104-115 was modified by addition of an N-terminal cysteine moiety for conjugation to carrier, and replacement of internal cysteine-112 moiety to avoid formation of internal disulphide bonds.

Immunogen #2: KKLEKVKAYR-C(SEQ ID NO: 42) (Amino Acid Sequence 77-86; "AUG2-KKLE" ('KKLE' disclosed as SEQ ID NO: 45)). A peptide corresponding to a segment of human 14-3-3 eta residues 77-86 was modified by addition of a C-terminal cysteine moiety for conjugation to carrier.

Immunogen #3: C-KNSVVEASEAAYKEA (SEQ ID NO: 43) (Amino Acid Sequence 143-157; "AUG3-CKNS" ('CKNS' disclosed as SEQ ID NO: 46)). A peptide corresponding to a segment of human 14-3-3 eta residues 143-157 was modified by addition of an N-terminal cysteine moiety for conjugation to carrier.

Immunogen #4: Full length human recombinant 14-3-3 eta (SEQ ID NO: 35), Protein Accession #: NP_003396.

Immunization

Figure 2:
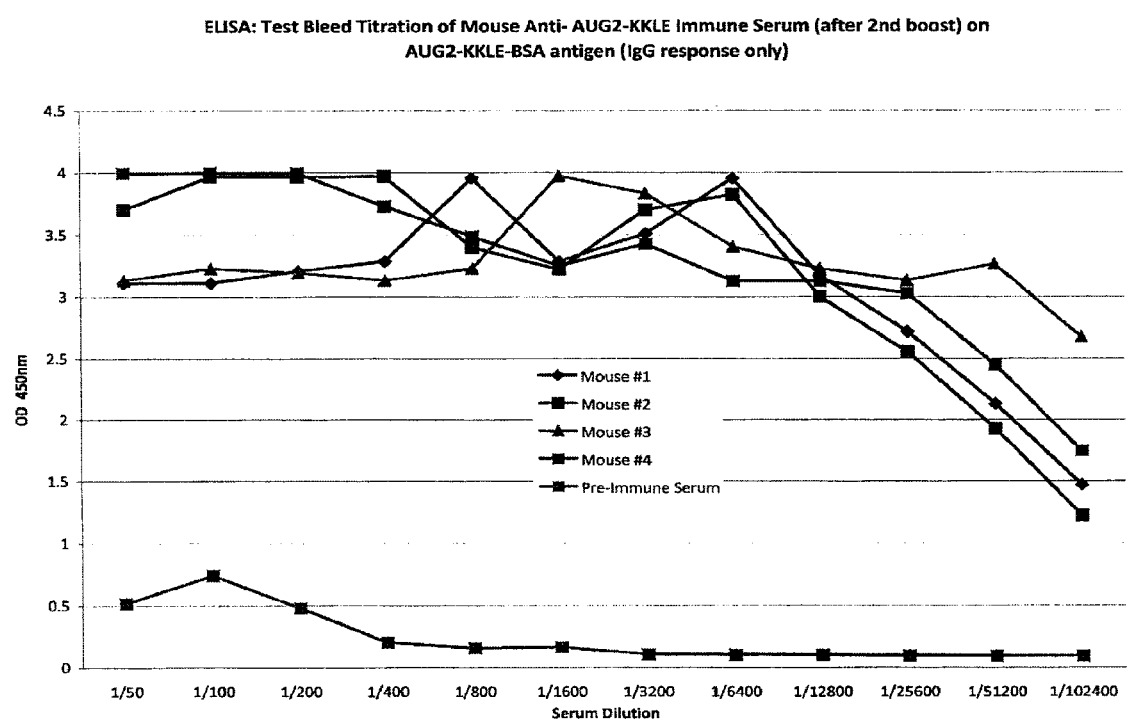
FIG. 2. ELISA: Test Bleed Titration of Mouse Anti-AUG2-KKLE Immune Serum (after 2nd boost) on AUG2-KKLE-BSA antigen (IgG response only) ('KKLE' disclosed as SEQ ID NO: 45).
Figure 3:
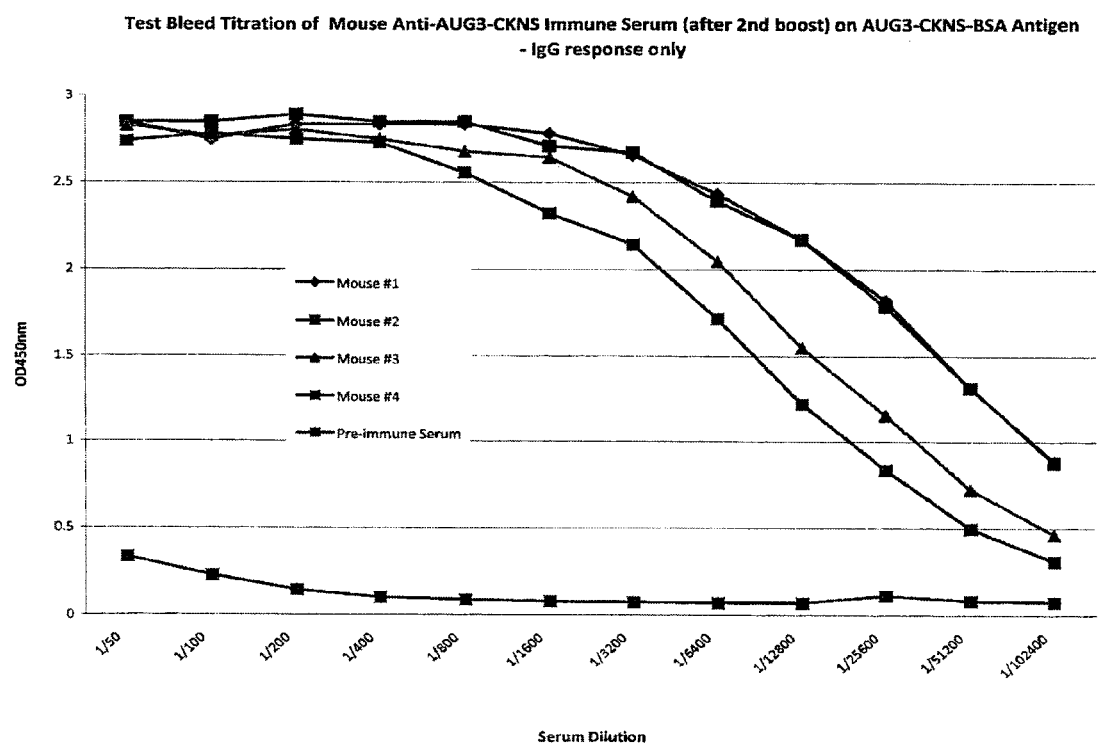
FIG. 3. ELISA: Test Bleed Titration of Mouse Anti-AUG3-CKNS Immune Serum (after 2nd boost) on AUG3-CKNS-BSA Antigen (IgG response only)('CKNS' disclosed as SEQ ID NO: 46).
Figure 5:
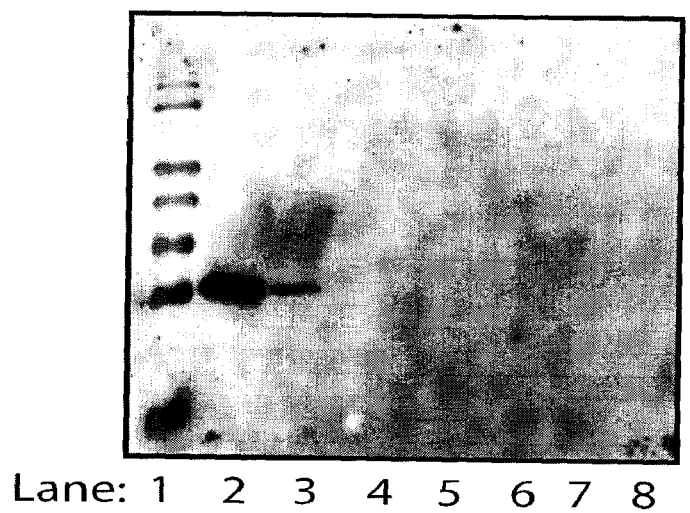
FIG. 5. Western Blot showing cross reactivity of a commercially available 14-3-3 eta polyclonal antibody against the seven isoforms of 14-3-3 proteins.
Figure 8:
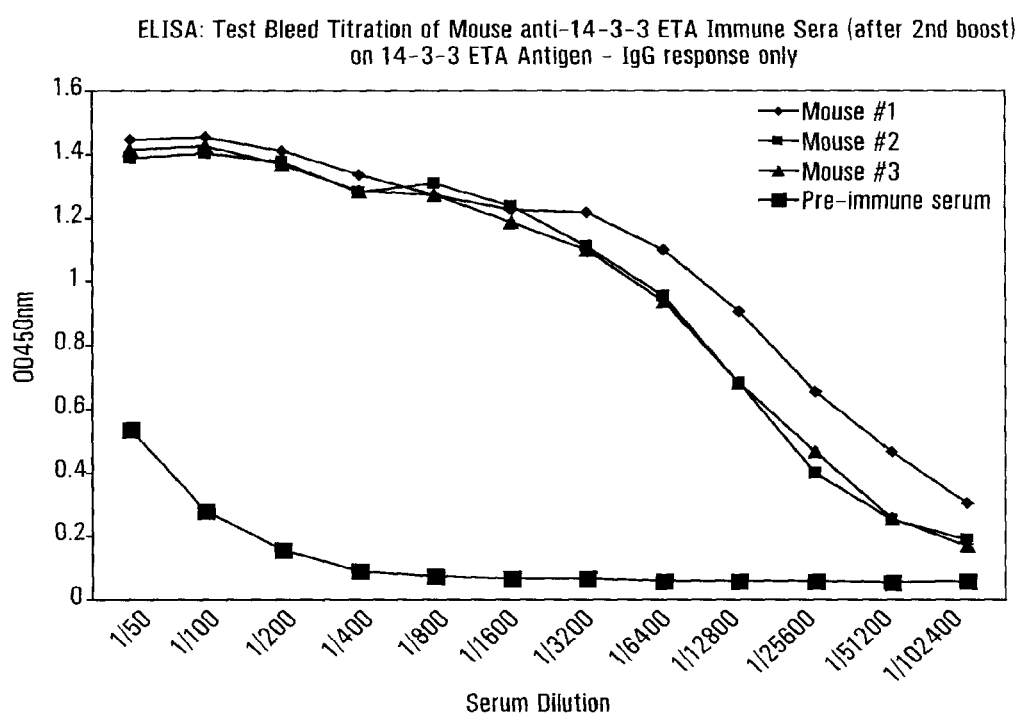
FIG. 8. ELISA: Test Bleed Titration of Mouse anti-14-3-3 eta Immune Sera (after 2nd boost) on 14-3-3 eta Antigen (IgG response only)

Groups of 4 female BALB/c mice were initially immunized by intraperitoneal injections using 50 ug of antigen (Immunogen #1, #2, #3 or #4) per mouse in Complete Freund's Adjuvant. Four subsequent boosts were administered as above, spaced at 3 week intervals, with antigen in Incomplete Freund's Adjuvant. When the serum titre had risen more than 10-fold from the pre-immune serum sample, as determined by ELISA, the 2 highest responders in each group were each boosted intravenously with 10 ug of antigen in 100 ul of sterile PBS pH 7.4. The titrations of serum samples from the immunized mice taken after the second boost are shown in FIG. 1 (Immunogen #1; CLDK (SEQ ID NO: 44)), FIG. 2 (Immunogen #2; KKLE (SEQ ID NO: 45)) FIG. 3 (Immunogen #3; CKNS (SEQ ID NO: 46)), and FIG. 8 (Immunogen #4).

Fusion Method

Three days after the final boost, the donor mice were sacrificed and the spleen cells were harvested and pooled. Fusion of the splenocytes with SP2/0 BALB/c parental myeloma cells was performed as previously described (Kohler et al., infra), except that one-step selection and cloning of the hybridomas was performed. Clones were picked 11 days post fusion and resuspended in wells of 96-well tissue culture plates in: 200 µl of D-MEM medium containing 1% hypoxanthine/thymidine, 20% fetal bovine serum, 2 mM GlutaMax I, 1 mM Sodium Pyruvate, 50 µg/ml Gentamycin, 1% OPI and 0.6 ng/ml IL-6. After 4 days, the supernatants were screened by ELISA for antibody activity on plates coated with 1 ug/well of purified antigen.

Procedure for Revival of Slow Growing Hybridoma Clones

Hybridoma cell lines that were growing slowly or looked unhealthy could usually be rescued by the addition of a rich growth media containing: D-MEM medium with 1% hypoxanthine/thymidine, 20% fetal bovine serum, 2 mM GlutaMax I, 1 mM Sodium Pyruvate, 50 µg/ml Gentamycin, 1% OPI, 20% conditioned EL-4 tissue culture supernatant and 0.6 ng/ml IL-6. EL-4 is a murine thymoma cell line, which when stimulated with phorbal 12-myristate 12-acetate (PMA, from Sigma, cat #P-8139) causes the cells to secrete interleukin 2 (IL-2), a B cell differentiating factor (EL-BCDF-nak), and two B cell growth factors (BSF-p1 and EL-BCGF-swa) and other additional lymphokines, which greatly enhance lymphocyte growth and differentiation. See G. Kohler, and C. Milstein, Preparation of monoclonal antibodies, Nature 25 (1975) 256-259; Ma, M., S. Wu, M. Howard and A. Borkovec. 1984. Enhanced production of mouse hybridomas to picomoles of antigen using EL-4 conditioned media with an in vitro immunization protocol. In Vitro 20:739.

After 30 days of stability testing, a total of 100 viable clones were obtained that secreted IgG capable of recognizing recombinant 14-3-3 eta. For the purposes of identifying lead clones to pursue, the 100 viable clones were screened using a series of methods including: immunoblotting (dot blot), a trapping assay and a custom capture (sandwich)

ELISA. All 100 clones were also tested for cross-reactivity using the custom capture (sandwich) ELISA with the other six 14-3-3 isoforms.

Example 2

Testing the Cross-Reactivity of Tissue Culture (TC) Supernatants from Hybridoma Clones Using Biotinylated 14-3-3 Isoforms as Bait in a Capture ELISA We have utilized a custom capture ELISA using the seven 14-3-3 isoforms as "bait" to determine whether any of the hybridoma clones that we have produced cross-react or recognize any of the six isoforms other than 14-3-3 Eta (η). As is evidenced by the representative data presented in Table 4, four of the selected hybridoma clones (AUG3-CKNS-2D5 ('CKNS' disclosed as SEQ ID NO: 46), AUG3-CKNS-7F8('CKNS' disclosed as SEQ ID NO: 46), AUG3-CKNS-7H8 ('CKNS' disclosed as SEQ ID NO: 46), AUG4-ETA-8F10) bind to and recognize 14-3-3 Eta at two serial dilutions, but do not bind with or cross-react with any of the other 14-3-3 isoforms, even at the lower dilution tested. This data clearly demonstrates that these clones are highly specific for 14-3-3 Eta (η). By contrast, one clone, AUG3-CKNS-4F10 ('CKNS' disclosed as SEQ ID NO: 46), binds with or cross-reacts with three other 14-3-3 isoforms, mainly 14-3-3 gamma, beta and zeta respectively. Taken together, these data indicate that our capture ELISA represents an effective method for identifying hybridoma clones which are highly specific for the 14-3-3 Eta (η) isoform.

The Custom Capture ELISA experiment in Table 4 was carried out as follows. ELISA plates were coated with neat overgrown TC supernatant at 100 μL/well and incubated overnight at 4° C. Biotin-labeled 14-3-3 (corresponding to all seven isoforms) was titrated from 1/500 to 1/16000 overtop and incubated for 1 hour at room temperature. Plates were then blocked with 3% skim milk powder in PBS (pH 7.4) at 100 μL/well and incubated for 1 hour at room temperature. 1/8000 Streptavidin-HRPO was diluted in PBS-Tween, added at 100 μl/well and incubated for 1 hour at 37° C. with shaking. TMB buffer was added at 50 μL per well and incubated in the dark at room temperature. Reactions were stopped with 50 μL 1M HCl per well after 10 minutes and read at OD450 nm.

TABLE 4a

Testing Cross-reactivity by ELISA (Table 4a discloses 'CKNS' as SEQ ID NO: 46)

Testing the cross-reactivity of tissue culture (TC) supernatants from hybridoma clones using biotinylated 14-3-3 isoforms as bait in a capture ELISA (measured at $OD_{450}$ nm)

| | 14-3-3 Isoform: | | | | | | | | | | | | | |
|---|---|---|---|---|---|---|---|---|---|---|---|---|---|---|
| | Gamma (γ) | | Beta (β) | | Sigma (σ) | | Theta/Tau (θ) | | Zeta (ζ) | | Epsilon (ε) | | Eta (η) | |
| TC supernatant: | 1:1500 | 1:3000 | 1:1500 | 1:3000 | 1:1500 | 1:3000 | 1:1500 | 1:3000 | 1:1500 | 1:3000 | 1:1500 | 1:3000 | 1:1500 | 1:3000 |
| AUG3-CKNS-2D5 | 0.076 | 0.073 | 0.085 | 0.075 | 0.084 | 0.076 | 0.101 | 0.082 | 0.097 | 0.076 | 0.074 | 0.064 | 0.351 | 0.263 |
| *AUG3-CKNS-4F10 | 0.084 | 0.076 | 0.096 | 0.085 | 0.125 | 0.102 | 0.185 | 0.153 | 0.167 | 0.122 | 0.139 | 0.101 | 0.114 | 0.09 |
| AUG3-CKNS-7F8 | 0.072 | 0.067 | 0.078 | 0.076 | 0.083 | 0.076 | 0.116 | 0.104 | 0.093 | 0.084 | 0.089 | 0.076 | 0.946 | 0.741 |
| AUG3-CKNS-7H8 | 0.07 | 0.066 | 0.072 | 0.063 | 0.087 | 0.078 | 0.098 | 0.083 | 0.089 | 0.08 | 0.074 | 0.064 | 0.774 | 0.608 |
| AUG4-ETA-8F10 | 0.072 | 0.069 | 0.073 | 0.069 | 0.092 | 0.084 | 0.109 | 0.097 | 0.099 | 0.082 | 0.099 | 0.09 | 0.169 | 0.131 |
| pre-immune serum (1:250) | 0.097 | 0.074 | 0.093 | 0.081 | 0.136 | 0.113 | 0.193 | 0.158 | 0.152 | 0.119 | 0.144 | 0.115 | 0.152 | 0.11 |

*control antibody

TABLE 4b

Testing Cross-reactivity by ELISA (background (pre-immune serum) values subtracted out) (Table 4b discloses 'CKNS' as SEQ ID NO: 46)

Testing the cross-reactivity of tissue culture (TC) supernatants from hybridoma clones using biotinylated 14-3-3 isoforms as bait in a capture ELISA (measured at $OD_{450}$ nm)

| | 14-3-3 Isoform: | | | | | | | | | | | | | |
|---|---|---|---|---|---|---|---|---|---|---|---|---|---|---|
| | Gamma (γ) | | Beta (β) | | Sigma (σ) | | Theta/Tau (θ) | | Zeta (ζ) | | Epsilon (ε) | | Eta (η) | |
| TC supernatant: | 1:1500 | 1:3000 | 1:1500 | 1:3000 | 1:1500 | 1:3000 | 1:1500 | 1:3000 | 1:1500 | 1:3000 | 1:1500 | 1:3000 | 1:1500 | 1:3000 |
| AUG3-CKNS-2D5 | −0.021 | −0.001 | −0.008 | −0.006 | −0.052 | −0.037 | −0.092 | −0.076 | −0.055 | −0.043 | −0.070 | −0.051 | 0.199 | 0.153 |
| *AUG3-CKNS-4F10 | −0.013 | 0.002 | 0.003 | 0.004 | −0.011 | −0.011 | −0.008 | −0.005 | 0.015 | 0.003 | −0.005 | −0.014 | −0.038 | −0.020 |

TABLE 4b-continued

Testing Cross-reactivity by ELISA (background (pre-immune serum) values subtracted out) (Table 4b discloses 'CKNS' as SEQ ID NO: 46)

Testing the cross-reactivity of tissue culture (TC) supernatants from hybridoma clones using biotinylated 14-3-3 isoforms as bait in a capture ELISA (measured at $OD_{450}$ nm)

14-3-3 Isoform:

| TC supernatant: | Gamma (γ) | | Beta (β) | | Sigma (σ) | | Theta/Tau (θ) dilution: | | Zeta (ζ) | | Epsilon (ε) | | Eta (η) | |
|---|---|---|---|---|---|---|---|---|---|---|---|---|---|---|
| | 1:1500 | 1:3000 | 1:1500 | 1:3000 | 1:1500 | 1:3000 | 1:1500 | 1:3000 | 1:1500 | 1:3000 | 1:1500 | 1:3000 | 1:1500 | 1:3000 |
| AUG3-CKNS-7F8 | −0.025 | −0.007 | −0.015 | −0.005 | −0.053 | −0.037 | −0.077 | −0.054 | −0.059 | −0.035 | −0.055 | −0.039 | 0.794 | 0.631 |
| AUG3-CKNS-7H8 | −0.027 | −0.008 | −0.021 | −0.018 | −0.049 | −0.035 | −0.095 | −0.075 | −0.063 | −0.039 | −0.070 | −0.051 | 0.622 | 0.498 |
| AUG4-ETA-8F10 | −0.025 | −0.005 | −0.020 | −0.012 | −0.044 | −0.029 | −0.084 | −0.061 | −0.053 | −0.037 | −0.045 | −0.025 | 0.017 | 0.021 |

*control antibody

Example 3

Cross Reactivity of Commercially Available Anti-14-3-3 Eta Polyclonal Antibody Commercially available anti-14-3-3 rabbit polyclonal antibody raised against a 12 amino acid peptide (Ac-DREQLLQRARLA-NH2 (SEQ ID NO: 47)) epitope from the N-terminus of 14-3-3 eta (Biomol International LP, Cat. SA476-0100 was used to evaluate the specificity of the antibody. Briefly, 1 μg human recombinant 14-3-3 eta, gamma, sigma, apha/beta, epsilon, theta or zeta were resolved by SDS-PAGE and probed with the anti-14-3-3 eta antibody.

In marked contrast to the results obtained with the antibodies of the present invention, the results in FIG. 4 show that this commercially available antibody against 14-3-3 eta cross reacted with other 14-3-3 isoforms, primarily gamma. Lane 1: Molecular Weight Standards; Lane 2: recombinant 14-3-3 eta; Lane 3: recombinant 143-3 gamma; Lane 4: recombinant 14-3-3 sigma; Lane 5: recombinant 14-3-3 alpha/beta; Lane 6: recombinant 14-3-3 epsilon; Lane 7: recombinant 14-3-3 theta; Lane 8: recombinant 14-3-3 zeta.

Example 4

Figure 6:
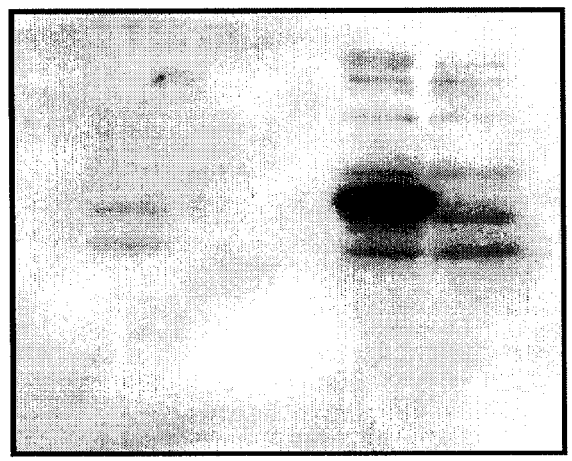
FIG. 6. Western Blot showing cell lysate-derived 14-3-3 eta protein and human recombinant 14-3-3 eta immunoprecipated by monoclonal antibody raised against full length human recombinant 14-3-3 eta.

Immunoprecipitation of Human Recombinant 14-3-3 Eta and Endogenous 14-3-3 Eta from HeLa Cells Monoclonal anti-14-3-3 antibodies from Example 1 were tested for their ability to immunoprecipitate or "capture" both recombinant and endogenous cellular 14-3-3 eta. For the therapeutic methods of the invention described herein, it is preferable to use antibodies that have the ability to immunoprecipitate or recognize 14-3-3 eta in its native 3-D configuration. Culture supernatants from anti 14-3-3 eta hybridoma clones were incubated at 4° C. for 2 hours with either buffer containing 100 ng human recombinant 14-3-3 eta, or buffer containing supernatant (200 μg protein) from lysed HeLa cells. immunoprecipitates were collected with Protein A/G agarose using standard methodology. Immunoprecipitates were analysed by SDS-PAGE and Western Blotting. FIG. 6 shows a Western Blot obtained using Hybridoma clone 7B11, which was made using Immunogen #4 (full length recombinant 14-3-3 eta. Lane 1: Protein A/G agarose beads alone; Lane 2: Protein A/G agarose beads were mixed with cell lysate; Lane 3: Protein A/G agarose beads were mixed with recombinant human 14-3-3 eta; Lane 4: Protein A/G agarose beads were mixed with hybridoma supernatant; Lane 5: Protein A/G agarose beads were mixed with hybridoma supernatant and cell lysate; Lane 6: Protein A/G agarose beads were mixed with hybridoma supernatant and recombinant 14-3-3 eta. The data show that clone 7B11 immunoprecipitated both HeLa cell-derived 14-3-3 eta (Lane 5) and human recombinant 14-3-3 eta (Lane 6).

Figure 7:
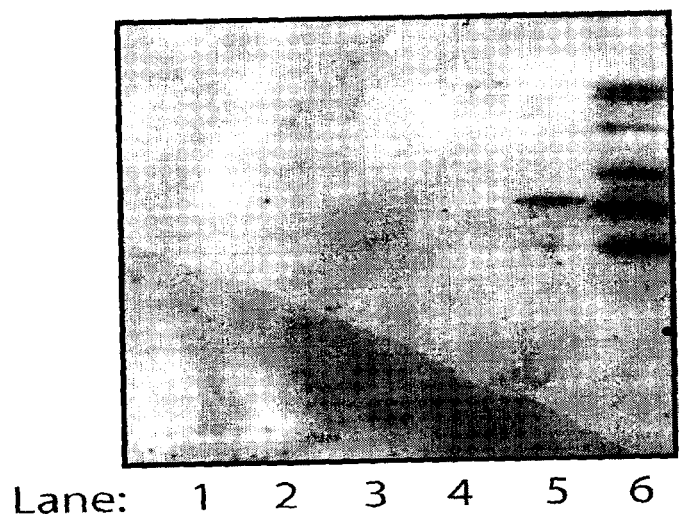
FIG. 7. Western Blot showing cell lysate-derived 14-3-3 eta protein and human recombinant 14-3-3 eta immunoprecipated by monoclonal antibody raised against a human 14-3-3 eta peptide fragment 142-158 SEQ ID NO:24 from a non-helical region of the protein.

FIG. 7 shows a Western Blot obtained by using hybridoma clone 2D5 made against Immunogen #3 (CKNS (SEQ ID NO: 46)). Lane 1: Protein A/G agarose beads alone; Lane 2: Protein A/G agarose beads were mixed with cell lysate; Lane 3: Protein A/G agarose beads were mixed with recombinant human 14-3-3 eta; Lane 4: Protein A/G agarose beads were mixed with hybridoma supernatant; Lane 5: Protein A/G agarose beads were mixed with hybridoma supernatant and cell lysate; Lane 6: Protein A/G agarose beads were mixed with hybridoma supernatant and recombinant 14-3-3 eta. The data show that clone 2D5 immunoprecipitated both HeLa cell lysate-derived 14-3-3 eta (Lane 5) and human recombinant 14-3-3 eta (Lane 6).

Similar analyses were performed for several other hybridoma clones (data not shown). These experiments demonstrate that the monoclonal antibodies produced in Example 1 are capable of binding to and immunoprecipitating or "capturing" 14-3-3 eta in its native configuration, as evidenced by the immunoprecipitation of the protein from HeLa cell lysates.

Example 5

14-3-3 Expression in Synovial Fluid and Serum of RA Affected Patients

The levels of the different isoforms of 14-3-3 proteins—β, γ, ε, η, τ σ and ζ—in pooled patient synovial fluid (SF) and serum (PS) samples were analyzed by western analysis using keratinocyte cell lysate (K) as a positive control. Only the η and γ isoforms were detected in SF samples, and stained with greater intensity compared to PS. Articular joint synovial fluid samples from 17 RA patients who presented with active synovitis, but had not yet received anti-TNF therapies also exhibited consistent expression of the η isoform of 14-3-3 (data not shown). All patients had a disease activity score (DAS) greater than 6.0.

Example 6

MMP Expression in Patient Synovial Fluid Serum

To determine if these variations were correlated to those of MMP-1 and MMP-3 in the same synovial samples, a total of 12 RA synovial fluid samples and their matched serum samples were simultaneously evaluated for 14-3-3 η and γ as well as for MMP-1 and MMP-3 proteins. 14-3-3 η was detected in all samples. MMP-1 was detected in all samples, both SF and PS, while MMP-3 was more variable in the levels detected. The 14-3-3 γ isoform was also detected in patient synovial fluid and serum samples (data not shown).

The expression of MMP-1 and MMP-3 demonstrate significant correlation with the expression of the 14-3-3 η and γ isoforms in both synovial fluid and serum (Table 5).

TABLE 5

| | Correlation of MMP and 14-3-3 protein levels in serum and synovial fluid. | | | |
|---|---|---|---|---|
| | 14-3-3 η serum | 14-3-3 η Synovium | 14-3-3 γ serum | 14-3-3 γ synovium |
| MMP-1 | r = 0.62; p = 0.02 | r = 0.83; p = 0.03 | r = 0.77; p = 0.02 | r = 0.65; p = 0.03 |
| MMP-3 | r = 0.68; p = 0.01 | r = 0.77; p = 0.003 | r = 0.80; p = 0.03 | r = 0.76; p = 0.04 |

Example 7

Sensitivity of Western Blot Detection of 14-3-3 Protein in Patient Serum and Synovial Fluid Samples To determine the detection level of 14-3-3 n in synovial fluid and serum samples, samples from 12 RA-affected or normal patients were pooled, and limiting dilutions of the pooled samples were analyzed by western blot. 14-3-3 η was detectable over a range of dilutions—as low as 0.1 µl effective volume of synovial fluid and 1.0 µl effective volume of serum (data not shown).

2 µl of pooled normal serum (NS) or patient serum (PS) was run alongside known concentrations of recombinant 14-3-3 η, ranging from 0.05-2.0 µg. The 2 µl volume of NS and PS samples was estimated to have approximately 1-1.5 and 15-20 µg of 14-3-3 η, respectively (data not shown). This suggests that the level of 14-3-3 η occurs in about a 10-fold excess in the serum of RA affected patients, compared to normal patients.

For more details, and results, see Kilani et al., J. Rheumatology, 34:1650-1657, 2007.

Example 8

Anti-14-4-3 Antibody Reduces MMP Expression in Mouse RA Model

Collagen-induced arthritis is induced in Male DBA mice by injection of 100 µg of purified type II collagen emulsified in Freund's complete adjuvant at the base of the tail as described in Williams et al., PNAS, 89:9784-9788, 1992. Mice are inspected daily thereafter and mice that exhibit erythema and/or swelling in one of more limbs are assigned randomly to a treatment regimen with anti-14-3-3 eta antibody described herein or a placebo treatment. Alternatively, a treatment regimen is begun on the day prior to immunization with type II collagen. Various treatment regimens are implemented, using groups of 10 mice, as follows:

1) selected anti-14-3-3 eta antibodies obtained and purified from the hybridoma supernatants of Example 1 are administered at various dosages ranging from 0.10 to 20 mg/kg (a) intraperitoneally or (b) into the synovium, twice weekly.

(2) Placebo Treatment

The arthritis is monitored over a 20-day treatment period, and the following disease indices are evaluated.

Clinical score. Mouse limbs are assessed for swelling, erythema, joint rigidity, and paw swelling. The clinical indicia of arthritis is reduced in animals in which the treatment regimen has been efficacious, as compared to placebo controls.

14-3-3 eta, MMP-1 and/or MMP-3 expression in the synovium. Synovial samples are taken at various time points, and the 14-3-3 eta, MMP-1 and/or MMP-3 levels are determined. The levels of MMP-1 and MMP-3 are reduced in animals in which the treatment regimen has been efficacious, as compared to placebo controls.

Histopathological assessment. Arthritic paws are fixed, embedded in paraffin, sectioned and stained with hematoxylin and eosin for microscopic evaluation. The severity of arthritis in each joint is graded according to the following criteria: mild=minimal synovitis, cartilage loss, and bone erosions limited to discrete foci; moderate=synovitis and erosions present but normal joint architecture intact; severe=synovitis, extensive erosions, and joint architecture disrupted. The severity of arthritis detected by histopathology is reduced in animals in which the treatment regimen has been efficacious, as compared to placebo controls.

Example 9

Anti-14-4-3 Antibody Reduces MMP Expression in Rabbit RA Model Induced by Implantation of Cells Secreting IL-1

The 14-3-3 eta antibodies of the invention are evaluated in a rabbit model in which arthritis is induced by the implantation of 5×10⁵ IL-1 producing cells into the knee joints of New Zealand white rabbits as described in Yao et al., Arthritis Research & Therapy 2006, 8:R16, available online at http://arthritis-research.com/content/8/1/R16. Testing and evaluation is done essentially as described in Example 8.

Example 10

Anti-14-4-3 Antibody Reduces MMP Expression in RA Model

Experimental arthritis is induced in Brown Norway rats or in New Zealand white rabbits by the injection of recombinant 14-3-3 eta protein into the synovium of leg joints. Testing and evaluation is done essentially as described in Example 8.

Other models of rheumatoid arthritis (collagen-induced arthritis, "CIA") and experimental designs useful for the methods of the invention can be found for example, in the following references: Williams, Methods Mol Med. 2004; 98:207-16. Collagen-induced arthritis as a model for rheumatoid arthritis; Brand, Com. Med., 55:114-122, 2005;

Vierboom et al., Drug Discovery Today, 12:327-335, 2007; Sakaguchi et al., Curr. Opin. Immunol., 17:589-594, 2005.

Prior to commencing an initial therapeutic regimen in a particular animal model, it is preferable to first validate the model as an inflammatory disorder model involving 14-3-3 eta. Preferably, the levels of 14-3-3 eta and MMP, preferably MMP-1 and/or MMP-3, are determined to show elevation following the induction of experimental arthritis in the model.

General Methods

Western Blotting

Samples (synovial fluid or serum (2 µl of each), recombinant human 14-3-3 eta, cell lysates or cell-lysate immunoprecipitates) were subjected to SDS-PAGE analysis with 12-15% (wt/vol) acrylamide gel, and electrotransferred onto PVDF membranes. Non-specific proteins on membranes were blocked in 5% skim milk powder in PBS-0.1% Tween-20 overnight. Immunoblotting for Example 3 was performed using 2 µg/ml of 7 isoforms specific rabbit anti-human 14-3-3 polyclonal antibodies (Martin H, Patel Y, Jones D, Howell S, Robinson K and Aitken A 1993. Antibodies against the major brain isoforms of 14-3-3 protein. An antibody specific for the N-acetylated amino-terminus of a protein. FEBS Letters. 331:296-303). In some experiments, mainly Example 7, the antibodies from the hybridoma clones in Example 1 were used for the immunoprecipitation or 'capture' experiments. The immunprecipitates were resolved by SDS-PAGE and the membranes were blocked in skim milk and then incubated with primary 14-3-3 eta (1:1000, BioMol International SE-486) and then the appropriate secondary horseradish peroxidise conjugated anti-rabbit IgG or anti-mouse IgG antibodies (1:2500 dilution). Immunoreactive proteins were then visualized using the ECL plus western blotting detection system. Keratinocyte cell lysate (K), recombinant protein and/or HeLa cell lysate was used as a positive control. SF: synovial fluid; PS: patient serum.

Patient Samples

Synovial fluid was obtained from the knee joints of patients with active synovitis prior to the institution of anti-TNF therapeutics. All patients had a DAS score >6.0. Matched blood samples were obtained by standard venipuncture procedures. The clot was removed by centrifugation.

Recombinant 14-3-3 Eta cDNA for keratinocyte-derived 14-3-3 eta was prepared from total RNA extracted from human keratinocytes, cloned and expressed in *E. coli*, and affinity purified, following the methods described in Ghahary et al 2004 J Invest Dermatol 122:1188-1197 (REF 36, infra). Primers used for PCR amplification of the 14-3-3 eta cDNA were

```
(GCGAATTCCTGCAGCGGGCGCGGCTGGCCGA
(SEQ ID NO: 48))
and (GCTCGAGCCTGAAGGATCTTCAGTTGCCTTC
(SEQ ID NO: 49)).
```

Untagged Recombinant 14-3-3 Proteins cDNA was derived from a human source, cloned and expressed in *E. coli*, and affinity purified. Primers used for the PCR amplification of the 14-3-3 eta cDNA were:

```
(agaattcagttgccttctcctgctt (SEQ ID NO: 50))
and (acatatgggggaccggga (SEQ ID NO: 51)); for 14-3-3
gamma
```

```
(agaattcttaattgttgccttcgccg (SEQ ID NO: 52))
and (acatatggtggaccgcgagc (SEQ ID NO: 53));
for 14-3-3 beta (acatatgacaatggataaaagtgagctg (SEQ ID NO: 54))
and (agaattcttagttctctccctccccagc (SEQ ID NO: 55));
for 14-3-3 epsilon (acatatggatgatcgagaggatctg (SEQ ID NO: 56))
and (agaattctcactgattttcgtcttccac (SEQ ID NO: 57));
for 14-3-3 sigma (acatatggagagagccagtctgatcc (SEQ ID NO: 58))
and (agaattcagctctgggctcctg (SEQ ID NO: 59));
for 14-3-3 theta (acatatggagaagactgagctgatcc (SEQ ID NO: 60))
and (agaattcttagttttcagccccttctgc (SEQ ID NO: 61));
for 14-3-3 zeta (acatatggataaaaatgagctggttc (SEQ ID NO: 62))
and (agaattcttaattttcccctccttctcct (SEQ ID NO: 63)).
```

ELISA Assay Conditions

For screening and testing: For screening and testing, 1.0 pg/well of anti-AUG1-CLDK ('CLDK' disclosed as SEQ ID NO: 44), anti-AUG2-KKLE ('KKLE' disclosed as SEQ ID NO: 45), anti-AUG3-CKNS ('CKNS' disclosed as SEQ ID NO: 4AI or anti-14-3-3 eta antigen was coated onto ELISA plates in dH2O at 50 µL/well and dried down overnight at 37° C. Testing on 14-3-3 ETA antigen 0.25 ug/well was coated in carbonate coating buffer and incubated at 4° C. overnight.

For testing by antibody trapping assay: 1/10000 Goat anti-mouse IgG/IgM trapping antibody (Pierce cat #31182) was coated onto ELISA plate in carbonate coating buffer (pH 9.6) at 100 µL/well incubated overnight at 4° C.

For testing on negative control antigen: 0.5 µg/well HT (human transferrin) antigen was coated onto ELISA plate in dH$_2$O at 50 µL/well and dried down overnight at 37° C.

For testing by Capture ELISA: ELISA plate was coated with neat overgrown TC sup at 100 µL/well incubated overnight at 4° C. Biotin labeled 14-3-3-ETA (or one of the six other 14-3-3 family members) was titrated from 1/500 to 1/16000 overtop and incubated for 1 hour at room temperature.

Blocking: Plates were blocked with 3% skim milk powder in PBS (pH 7.4) at 100 µL/well and incubated for 1 hour at room temperature.

1° antibody: Mouse anti-AUG1-CLDK ('CLDK' disclosed as SEQ ID NO: 4A, anti-AUG2-KKLE ('KKLE' disclosed as SEQ ID NO: 45), anti-AUG3-CKNS ('CKNS' disclosed as SEQ ID NO: 46) or anti-14-3-3 eta hybridoma tissue culture supernatant and mouse monoclonal controls were added at 100 µL neat per well for screening and testing. Mouse anti-AUG1-CLDK ('CLDK' disclosed as SEQ ID NO: 44), anti-AUG2-KKLE ('KKLE' disclosed as SEQ ID NO: 45), anti-AUG3-CKNS ('CKNS' disclosed as SEQ ID NO: 46) or anti-14-3-3 eta immune serum and mouse pre-immune serum were diluted 1/500 in SP2/0 tissue culture supernatant added at 100 μL/well for screening and testing. Incubated for 1 hour at 37° C. with shaking for both the screening and testing.

2° antibody used for screening and testing: 1/25000 Goat anti-mouse IgG Fc HRP conjugated (Jackson cat #115-035-164) was used in screening and testing. Secondary antibody diluted in PBS-Tween added at 100 μL/well and incubated for 1 hour at 37° C. with shaking.

Streptavidin Used for Capture ELISA:

Added 100 ul/well of Streptavidin HRPO (1:8000, Cedar-Lane cat #CLCSA1007) and incubated for 1 hour at room temperature with shaking.

Substrate: TMB buffer (BioFx cat #TMBW-1000-01) was added at 50 μL per well and incubated in the dark at room temperature. Reactions for screening and testing were stopped with 50 μL 1M HCl per well after 10 minutes and read at $OD_{450}$ nm.

Dot Blot Conditions:

For Screening: Millipore, Immobilon Transfer Membrane cat #IPVH304F0 was used. 14-3-3 ETA antigen was boiled in sample buffer 5 minutes and allowed to cool. Antigen was dotted on for a total of 6 μg dot amounts with a pipettor. After allowing antigen to dry for 15 minutes blots were washed with several changes of PBS-Tween pH7.4. Blots were kept in separate petri dishes for entire screening process.

Blocking: The PVDF membrane was blocked with 5% milk powder in PBS (pH 7.4) for 1 hour at room temperature. Blot was washed after blocking for 15 minutes with several changes of PBS-Tween pH7.4. Blots were allowed to dry on paper towels face up for 10 minutes prior to primary antibody application.

1° antibody: Mouse AUG1-CLDK ('CLDK' disclosed as SEQ ID NO: 44), anti-AUG2-KKLE ('KKLE' disclosed as SEQ ID NO: 45), anti-AUG3-CKNS ('CKNS' disclosed as SEQ ID NO: 46) or anti-14-3-3 eta hybridoma tissue culture supernatant and mouse monoclonal controls were incubated with blots in separate petri dishes. Mouse anti-AUG1-CLDK ('CLDK' disclosed as SEQ ID NO: 44), anti-AUG2-KKLE ('KKLE' disclosed as SEQ ID NO: 45), anti-AUG3-CKNS ('CKNS' disclosed as SEQ ID NO: 46) or anti-14-3-3 eta immune and mouse pre-immune sera were diluted 1/500 in SP2/0 tissue culture supernatant used as controls. Blots were incubated with shaking for 1 hour at room temp. Blots were washed after primary antibody incubation for 30 minutes with 5 changes of PBS-Tween pH7.4.

2° antibody: 1/5000 Goat anti-mouse IgG/IgM, (H+L), Alkaline Phosphatase Conjugated (Rockland 610-4502) diluted in PBS-Tween pH 7.4 was added to the blots and incubated with shaking in Petri dishes for one hour at room temperature. Blots were washed after secondary antibody incubation for 30 minutes with 5 changes of PBS-Tween pH7.4. Blots were equilibrated in Tris 0.1M pH 9 buffer for 10 minutes at room temp and then dripped dried before addition of substrate.

Substrate: BCIP/NBT developer 1 component AP membrane substrate (BioFX product #BCID-1000-01) was dripped onto blot neat at room temp. The reaction was stopped after 5 minutes with cold tap water and results were determined quantitatively by eye and given a score of strong positive +++, moderate positive ++, weak positive +, slight positive +/−, negative −.

REFERENCES

1. Harris E D Jr., History and Epidemiology of Rheumatoid Arthritis: How long has it affected us, and who is at risk? In: Rheumatoid Arthritis. Philadelphia: W.B. Saunders Company, 1997: 21-27.
2. Harris E D Jr., Introduction. In: Rheumatoid Arthritis. Philadelphia: W.B. Saunders Company, 1997: xix-xxiii.
3. Harris E D Jr., Rheumatoid Synovium: Complex, and More Than the Sum of its Parts. In: Rheumatoid Arthritis. Philadelphia: W.B. Saunders Company, 1997: 127-149.
5. Firestein G S. (1997). Rheumatoid synovitis and pannus. In: J. H. Klippel and P. A. Dieppe, Editors, Rheumatology, Mosby, London, pp. 5/13.1-5/13.5, 1997.
6. Pap T, Shigeyama Y, Kuchen S. (2000). Arthritis Rheum. 43: 1226-1232.
7. Tolboom T C A, Pieterman E, van der Laan W E. Ann. Rheum. Dis. 61: 975-980, 2002.
8. Sorsa T, Konttinen Y T, Lindy O. Arthritis Rheum. 22: 44-53, 1992.
9. Lindy O, Konttinen Y T, Sorsa T. Arthritis Rheum. 40:1391-1399, 1997.
10. Ahrens D, Koch A E, Pope R M. Arthritis Rheum. 39:1576-1587, 1996.
11. Smeets T J M, Dayer J M, Karan M C. Arthritis Rheum. 43:270-274, 2000.
12. Poole A R; Cartilage in health and disease. In: Koopman W J. Ed. Arthritis and Allied conditions. A textbook of rheumatology. 14th ed. Baltimore: Williams and Wilikins, 2001: 226-284.
13. Konttinen Y T, Ceponis A, Takagi M, Ainola M, Sorsa T, Sutinen M, et al. Matrix Biol. 17:585-601, 1998.
14. Katrib. A, McNeil H P, Youssef P P: Inflamm. Res. 51: 170-175, 2002.
15. Harris E D Jr., Cytokines, Lymphokines, Growth Factors, and Chemokines. In: Rheumatoid Arthritis. Philadelphia: W.B. Saunders Company, 1997: 105-125.
16. Jasser, M. Z., Mitchell P. G. and Cheung, H. S.: induction of stomelysin-1 and collagenases synthesis in fibrochondrocytes by TNF-alpha. Matrix Biology 14: 241, 1994.
17. Burger O, Rezzonico R, Li J M, Modoux C, Pierce R A, Welgus H G, Dayer J M. Arthritis Rheum. 41(10):1748-59, 1998
18. Y. Yamamura, R. Gupta, Y. Mont, X. He, R. Pai, J. Endres, A. Freiberg, K. Chung and D. A. Fox. J. Immunol. 166 (2001), pp. 2270-2275
19. Miranda-Carus M E, Balsa A, Benito-Miguel M, Perez de Ayala C, Martin-Mola E. J. Immunol. 173:1463-1476, 2004
20. Cho M L, Yoon C H, Hwang C Y. Arthritis Rheum. 50:776-784, 2004
21. Bombara M P, Webb D L, Conrad P. J. Leukocyte Biol. 54: 399-406, 1993.
22. McInnes I B, Leung B P, Liew F Y. Arthritis Res. 2(5):374-8.34, 2000.
23. F U H, Subramanian R R, Masters S C: Annu Rev Pharmacol Toxicol 40:617-647, 2000.
24. Hsich G, Kenney K, Gibbs C J, Lee K H, Harrington M G: N Engl J Med 335:924-30, 1996
25. Wilker E, Yaffe M B: J Mol Cell Cardiol 37: 633-642, 2004.
26. Moore et al. 1967.
27. Ichimura T, Isobe T, Okuyama T, Yamauchi T, Fujisawa H (1987) FEBS Lett. 219:79-82.
28. Ichimura T, Isobe T, Okuyama T, Takahashi N, Araki K, Kuwano R, Akahashi Y (1988). Proc Natl Acad Sci USA, 85:7084-8.
29. Toker A, Ellis C A, Sellers L A, Atiken A 1990. Eur J Biochem 191:421-429.
30. Craparo A, Freund R, Gustafson T (1997). J Biol Chem 272:11663-69.
31. Yaffe M B (2002). FEBS Lett 513(1):53-57.

32. Hermeking H, Lengauer C, Polyak K, He T C, Zhang L, Thiagalingam S, Kinzler K W, Volgelstein B. Mol Cell 1:3-11, 1997.
33. Chan T A, Hermeking H, Lengauer C, Kinzler K W, Volgelstein B. Nature 401:616-620, 1999.
34. Laronga C, Yang H Y, Neal C, Lee M H (2000). J. Biol. Chem. 275:23106-23112.
35. Wang B, Yang H, Liu Y, Jelinek T, Zhang L, Ruoslahti E, Fu H (1999) Biochemistry 38: 12499-12504.
36. Ghahary A, Karimi-Busheri F, Marcoux Y, Li Y, Tredget E E, Kilani R T, Li L, Zheng J, Karami A, Keller B, Weinfeld M. J. Invest. Dermatol. 122(5): 1188-1197, 2004.

All citations are expressly incorporated herein in their entirety by reference.

I claim:

1. A method for determining the presence of 14-3-3 eta protein in a sample, the method comprising:
  (a) contacting a sample with a first antibody, wherein the first antibody is an anti-14-3-3 eta antibody produced by hybridoma AUG3-CKNS-7F8, wherein the first antibody is immobilized on a solid support, wherein said first antibody is capable of specifically binding to a human 14-33 eta protein in its natural configuration and exhibits selectivity for said human 14-3-3 eta protein over other human 14-3-3 protein isoforms, and wherein said anti-14-3-3 eta antibody specifically binds to the amino acid sequence KNSVVEASEAAYKEA (SEQ ID NO: 32),
  (b) incubating under conditions such that 14-3-3 eta proteins within the sample are allowed to bind to the immobilized first antibody,
  (c) washing to remove unbound sample from the immobilized protein-antibody complexes,
  (d) contacting the sample bound to the immobilized first antibody with a second antibody capable of detecting the bound 14-3-3 eta protein, wherein the first and second antibodies are different,
  (e) incubating under conditions such that the second antibody is allowed to bind to the 14-3-3 eta proteins bound to the immobilized first antibody,
  (f) washing to remove unbound second antibody, and
  (g) determining the amount of second antibody that remains bound to the solid support.

2. The method according to claim 1, wherein said sample is a sample of a patient having arthritis or a patient having rheumatoid arthritis.

3. The method according to claim 1, wherein the sample is a sample of synovial fluid, plasma, or serum.

4. The method according to claim 1, wherein said second antibody is labeled with a detection reagent, and wherein said: d) determining the amount of second antibody that remains bound to the solid support comprises determining the amount of detection reagent that remains bound to the solid support.

5. The method according to claim 4, wherein the label is selected from the group consisting of radioactive groups, dyes, luminescent groups, fluorescent groups, biotin and enzyme reporter groups.

6. The method according to claim 4 or 5, further comprising comparing a detected level of the label with a standard whereby the amount of the 14-3-3 eta protein present in said sample may be determined.

7. The method according to claim 1, wherein said second antibody is produced by hybridoma AUG4-ETA-8F10.

8. The method of claim 1, wherein the method further comprises detecting at least one additional protein marker selected from the group consisting of a matrix metalloproteinase (MMP), an anti-cyclic citrullinated peptide (CCP), anti-rheumatoid factor (RF), and C-reactive protein (CRP).

9. The method of claim 8, wherein the at least one additional protein marker is anti-RF.

10. The method of claim 8, wherein the at least one additional protein marker is anti-CCP.

11. The method of claim 8, wherein the method comprises detecting anti-RF and anti-CCP.

12. The method of claim 8, wherein the at least one additional protein marker is an MMP.

13. The method of claim 12, wherein the method comprises detecting MMP-1 and/or MMP-3.

14. The method according to claim 1, wherein said sample is a sample of a patient having psoriasis or a patient having psoriatic arthritis.

15. The method according to claim 1, wherein said sample is a sample of a patient having lupus or a patient having Sjogren's Syndrome.

* * * * *